United States Patent [19]
Chapman et al.

[11] Patent Number: 5,948,385
[45] Date of Patent: Sep. 7, 1999

[54] ANTIMICROBIAL MATERIALS

[75] Inventors: John R. Chapman, Lake Villa; Ying-Cheng Lo, Green Oaks; Winnie Kubey, Buffalo Grove; Clifford J. Holmes, Glenview; David Bell, Grayslake, all of Ill.

[73] Assignee: Baxter International Inc., Deerfield, Ill.

[21] Appl. No.: 08/940,579

[22] Filed: Sep. 30, 1997

Related U.S. Application Data

[62] Division of application No. 08/723,380, Sep. 30, 1996.

[51] Int. Cl.$^6$ ................................................. A61K 51/00
[52] U.S. Cl. .................. 424/1.29; 424/1.33; 424/1.37; 424/404
[58] Field of Search .................. 424/404, 1.11, 424/1.29, 1.33, 1.37; 604/304, 89.1, 203

[56] References Cited

U.S. PATENT DOCUMENTS

| | | | |
|---|---|---|---|
| 4,011,312 | 3/1977 | Reuter et al. | 424/78 |
| 4,343,788 | 8/1982 | Mustacich et al. | 424/78 |
| 4,381,380 | 4/1983 | LeVeen et al. | 525/452 |
| 4,387,217 | 6/1983 | Schmolka | 528/417 |
| 4,876,331 | 10/1989 | Doi | 528/361 |
| 4,935,064 | 6/1990 | Robbins et al. | 134/2 |
| 4,968,439 | 11/1990 | LeVeen et al. | 210/764 |
| 4,990,144 | 2/1991 | Blott | 604/304 |
| 5,045,626 | 9/1991 | Koide et al. | 528/193 |
| 5,070,889 | 12/1991 | LeVeen et al. | 128/830 |
| 5,071,648 | 12/1991 | Rosenblatt | 424/78.06 |
| 5,156,164 | 10/1992 | LeVeen et al. | 128/832 |
| 5,176,665 | 1/1993 | Watanabe et al. | 604/317 |
| 5,344,411 | 9/1994 | Domb et al. | 604/265 |
| 5,437,656 | 8/1995 | Shikani et al. | 604/89.1 |
| 5,444,871 | 8/1995 | Lopez | 2/114 |
| 5,695,458 | 12/1997 | Shikani et al. | 604/4 |
| 5,733,270 | 3/1998 | Ling et al. | 604/32.6 |

FOREIGN PATENT DOCUMENTS

| | | |
|---|---|---|
| 0 048 286 | 3/1982 | European Pat. Off. . |
| 0 398 489 | 11/1990 | European Pat. Off. . |
| 56-41232 | 4/1981 | Japan . |
| 57-50906 | 3/1982 | Japan . |
| 58-167404 | 10/1983 | Japan . |
| 59-193189 | 11/1984 | Japan . |
| 60-232288 | 11/1985 | Japan . |
| 61-171403 | 8/1986 | Japan . |
| WO 83/03975 | 11/1983 | WIPO . |
| WO 91/04940 | 4/1991 | WIPO . |
| WO 92/15286 | 9/1992 | WIPO . |

OTHER PUBLICATIONS

Jansen et al., "In–Vitro Efficacy of a Central Venous Catheter Complexed with Iodine to Prevent Bacterial Colonization," *J. Antimicrob. Chemother.*, vol. 30, pp. 135–139 (1992).

Kristinsson et al., "Antimicrobial Activity of Polymers Coated with Iodine–Complexed Polyvinylpyrrolidone," *J. Biomater. Appl.*, vol. 5, pp. 173–184 (1991).

LeVeen et al., "The Mythology of Povidone–Iodine and the Development of Self–Sterilizing Plastics," *Surg. Gynecol. Obstet.*, vol. 176, pp. 183–190 (1993).

Pender et al., "Diffusion of Iodine into PE and PET," *Journal of Polymer Science*, vol. 21, No. 9, Sep. 1983, pp. 1635–1646.

*Primary Examiner*—Thurman K. Page
*Assistant Examiner*—Lakshmi Channavajjala
*Attorney, Agent, or Firm*—Thomas S. Borecki; Charles R. Mattenson; Robert M. Barrett

[57] ABSTRACT

An antimicrobial material incorporated with a molecular halogen is provided. The antimicrobial material includes a plastic material and a molecular halogen entrapped within the plastic material. A directional release material is also provided in the present application. The directional release material allows for the control of the rate and site of halogen release. Still further, method of impregnating a plastic material are also provided.

4 Claims, 7 Drawing Sheets

- □ LLDPE
- ◊ Polypropylene
- × Copolyester
- ○ Polycarbonate polyester
- ■ Polystryene

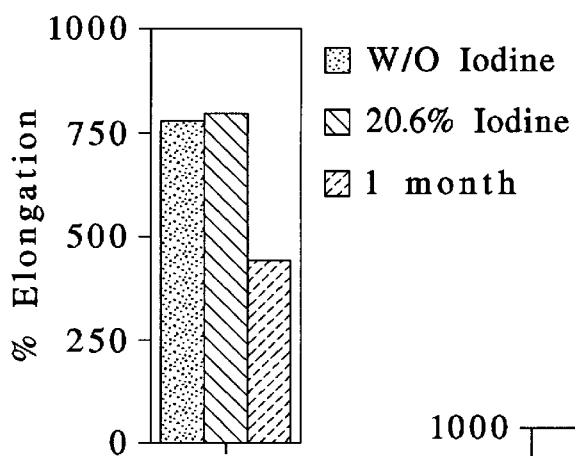
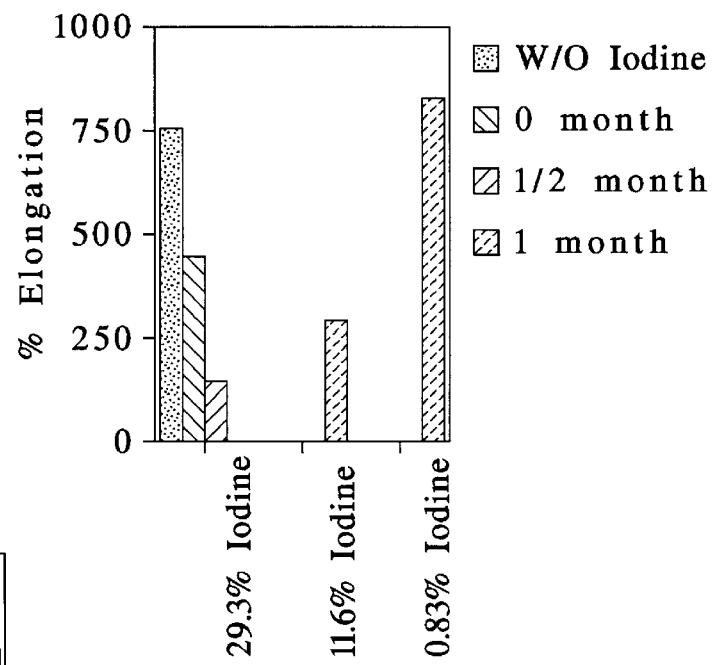
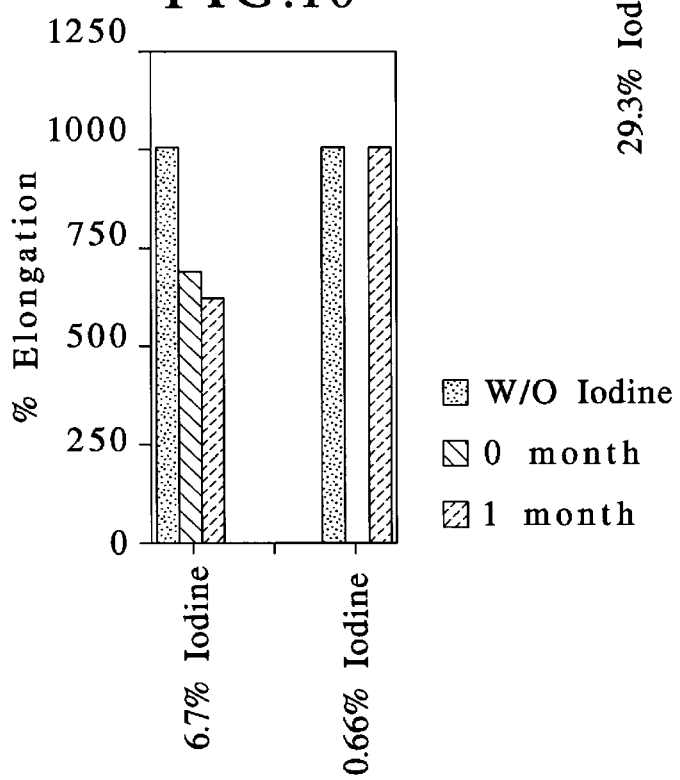

ANTIMICROBIAL MATERIALS

This is a division of application Ser. No. 08/723,380, filed on Sep. 30, 1996.

BACKGROUND OF THE INVENTION

The present invention relates generally to disinfectants and products having same. More specifically, the present invention relates to materials having antimicrobial properties and products made therefrom.

In the medical industry, one of the principal concerns with respect to products that are introduced into the body or provide a pathway into the body is bacterial infection. The industry continually strives to reduce the incidence of bacterial infection caused by bacteria contamination of medical apparatuses. This is particularly true in connection with medical apparatuses that cannot normally be sterilized in autoclaves or which when used encounter bacteria containing environments.

For example, sutures, catheters, surgical tape, tubings, sponges, gloves, pads, surgical covers, dialysis connectors, and certain medical instruments cannot be autoclaved to ensure sterility. They often must be used in areas where pathogenic bacteria are encountered. Accordingly, for such medical apparatuses, the art has long sought means and methods of rendering those medical apparatuses antibacterial and, hopefully, antimicrobial.

The general approach in the art has been that of coating the medical apparatuses, or a surface thereof, with a bactericide. However, since most bactericides are partly water soluble, or at least require sufficient solubilization for effective antibacterial action, simple coatings of the bactericides have been proven unreliable. For this reason, the art has sought to incorporate the bactericides into the medical apparatus or at least provide a stabilized coating thereon.

With the increased use of polymeric materials for construction of medical apparatuses, utilizing an antimicrobial polymer has become even more desirable. The art, therefore, has sought various combinations of plastics and antibacterial agents. The antibacterial agent could be fixedly attached to or incorporated in the plastic, so that the combination thereof could be used for the manufacture of these plastic medical apparatuses.

This relatively recent effort in the art has taken a myriad of different approaches. For example, U.S. Pat. No. 3,401,005, in an attempt to create a product that functions satisfactorily, applies a complexed composition of polyvinylpyrrolidone and iodine to cotton gauze. When dried, the coated material would have a germicidal characteristic. In a similar effort, a complexed composition of polyvinylpyrrolidone and iodine was placed in absorbable, gelatin foams to produce surgical sponges. In the '005 patent, iodine is complexed with polyvinylpyrrolidone. The complexed composition was found to release iodine under use conditions.

Solid polyvinylpyrrolidone complexed with iodine is disclosed in U.S. Pat. No. 3,898,326 as useful as a disinfectant material. U.S. Pat. No. 4,017,407 extends this complexed composition to include detergents.

U.S. Pat. No. 4,381,380 relates to a polymeric bacteriocidal composition for use in antibacterial applications. The composition of the '380 patent contains a plastic, sparingly cross-linked polyurethane having —O—(CO)—NH— urethane linkages and iodine complexed with a sufficient number of the linkages to provide bacteriocidal properties to the composition. Iodine solutions having concentrations of from 1% to 15% were utilized for complexing the iodine with the urethane linkages.

Utilizing a plastic completely complexed with iodine as a potential self-sterilizing material has disadvantages. Among other factors, the concentration of the iodine in the solution and the solvent of the iodine solution limits the amount of iodine completed with the polyurethane. Further, the rate of release of iodine from plastics complexed with iodine depends upon the affinity the plastic has for iodine. As a result, these complexed plastics often do not provide an effective delivery of iodine into the atmosphere or a liquid for sufficient antimicrobial treatment.

Therefore, a need exists for an improved antimicrobial material containing not only increased concentrations of a bacteriocidal substance, but also an effective and controlled delivery of the bacteriocidal substance.

SUMMARY OF THE INVENTION

The present invention provides an improved antimicrobial material including a plastic material and a molecular halogen entrapped within the plastic material. The molecular halogen is primarily absorbed into the plastic material and only some, if any, is complexed with the plastic material.

In an embodiment, approximately 0 to 40% of the molecular halogen is entrapped in the plastic material.

In a preferred embodiment, the molecular halogen is iodine.

The present invention also provides a directional release material that effectively allows for the control of the site and rate of halogen delivery. The directional release material includes a first plastic material having impregnated therein a halogen. The first plastic material and the halogen define an outer surface having a first release rate for the halogen. The directional release material also includes a second plastic material having impregnated therein the halogen. The second plastic material and the halogen define an inner surface having a second release rate for the halogen. This second release rate being faster than the first release rate to achieve directional release of the halogen.

In an embodiment, suitable plastic materials that may be used in the directional release material are: polycarbonate/polyester blend; polyethylene; polyurethane; polypropylene; polystyrene; copolyester; and styrene-ethylene-butylene-styrene copolymers.

Still further, the present invention provides a method for making a disinfectant material. The method includes the step of contacting a plastic material with a halogen gas that is absorbed in the plastic material.

In an embodiment, the method for making a disinfectant material includes the further step of forming the plastic material into a medical apparatus. Preferably, the plastic material is contacted with the halogen gas after being shaped into the medical apparatus.

The present invention also provides a method for impregnating a plastic material. The method includes the step of delivering iodine crystals in an enclosed vessel. Then, the plastic material to be impregnated is placed in the enclosed vessel for a time sufficient to allow iodine to absorb into the plastic material.

An advantage of the present invention is that it provides an improved antimicrobial material.

Another advantage of the present invention is that it provides the impregnation of halogen gases into a plastic material, resulting in an increased uptake of the molecular halogens.

Yet another advantage of the present invention is that it provides a directional release material that effectively allows for the control of the site and rate of halogen delivery.

Still further, an advantage of the present invention is that it provides an antimicrobial polymer that delivers a halogen for use as an antimicrobial substance in a controlled manner.

Moreover, an advantage of the present invention is that it provides a new method for impregnating a plastic material with iodine.

Additional features and advantages of the present invention are described in, and will be apparent from, the detailed description of the presently preferred embodiments and from the drawings.

BRIEF DESCRIPTION OF THE DRAWINGS

FIGS. 8–10 illustrate the effects of iodine on the elongation of various plastic materials.

DETAILED DESCRIPTION OF THE PRESENTLY PREFERRED EMBODIMENTS

Figure 1:
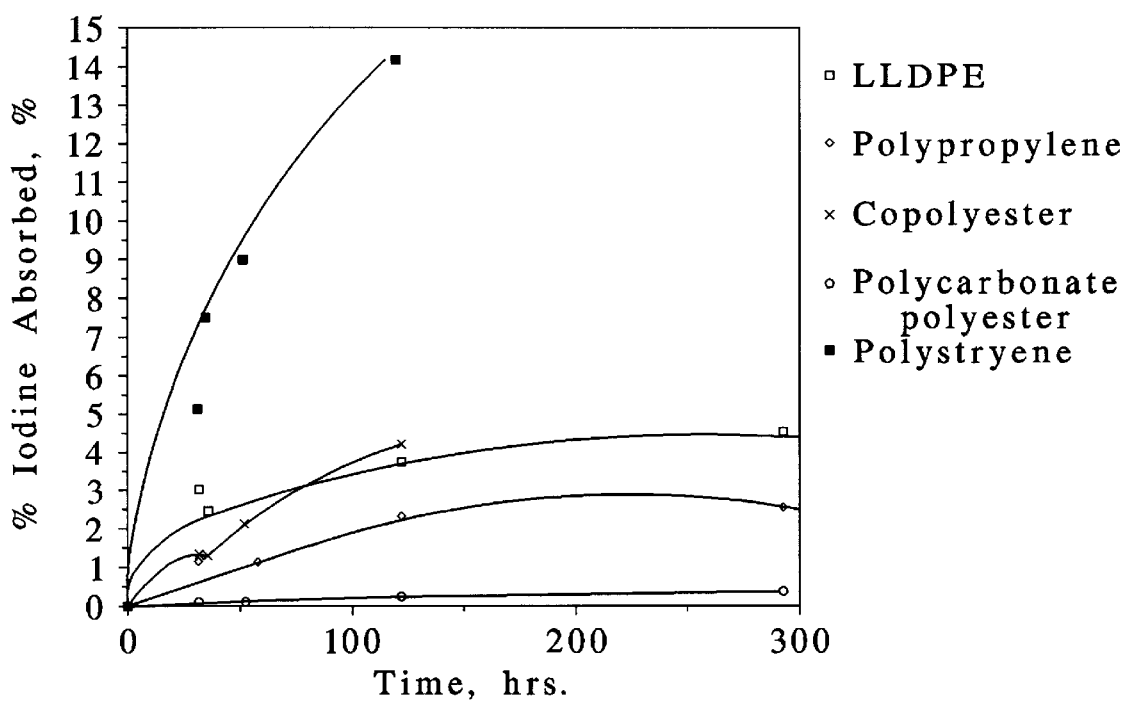
FIG. 1 illustrates the absorption rate by weight percent for various plastic samples treated pursuant to the present invention.

The present invention provides improved methods and materials for producing an antimicrobial material. Pursuant to the present invention, a molecular halogen is impregnated in a plastic material. Utilizing a halogen gas to impregnate plastic promotes the impregnation of larger amounts of molecular halogens than the amount that can be achieved using liquid halogens.

For illustrative purposes only, the detailed description focuses on the use of molecular iodine as a suitable halogen that may be used in the present invention. Iodine is a known microbicide, with a broad spectrum of action. However, as those skilled in the art will appreciate, other halogens, such as chlorine and bromine, are also suitable anti-bacterial agents. Therefore, the present invention encompasses the use of all such halogens.

The antimicrobial material of the present invention consists of a plastic material having a molecular halogen absorbed therein. To entrap the molecular halogen in the plastic material, a halogen gas, such as gaseous iodine, is contacted with the plastic material.

In one embodiment, elemental iodine is contacted with the plastic material. After the elemental iodine sublimes into iodine gas, molecular iodine is absorbed in the plastic material. Iodine is able to enter and leave the plastic material without losing its microbicidal activity.

Absorbing iodine gases into the plastic material differs from the prior treatments utilizing iodine solutions and, in fact, provides advantages over same. Pursuant to the present invention, molecular iodine is largely entrapped in the plastic material and only some, if any, of the iodine forms a chemical complex with such plastic material. The gradual release of such iodine depends on the mobility of molecular iodine gas in the plastic material.

A physical barrier, as opposed to the chemical barriers of prior treatments, prevents iodine's rapid release into the atmosphere or a liquid. Previously, researchers have focused on forming a chemical complex between iodine and the particular plastic material to achieve a disinfecting type apparatus. With these prior treatments, iodine is bound as a result of a specific affinity due to the molecular structure of the plastic material. This binding results from a bonding action that is unique to the specific plastic material and not based on iodine's solubility properties.

In contrast, the present invention takes advantage of the lipophilic nature of molecular iodine. This lipophilic nature allows molecular iodine to permeate into plastics in a reversible manner. The iodine embedded plastic allows the sustained delivery of iodine.

The rate of iodine delivery depends upon several factors. For example, such factors include, among others, iodine concentration, temperature, pressure, materials, surface area. Manipulation of these factors provides a basis for controlling iodine delivery to materials to be disinfected. For example, adding potassium iodide to aqueous solutions increases the rate at which iodine is released from the plastic material.

The selection of polymer or polymer formulations making up the plastic material allows control of the iodine uptake and release properties. The inventors have discovered that different plastics have different solubility properties for iodine. Some plastics will take up larger amounts of iodine than other plastics (e.g. polypropylene versus polystyrene) to create a larger reservoir for sustained delivery of iodine.

Plastic materials suitable in the present invention can be classified according to the following hierarchy:

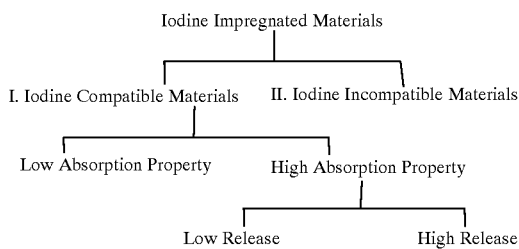

Examples of iodine incompatible materials include highly unsaturated materials (e.g., natural rubber), whereas saturated plastics or plastics with low levels of unsaturation are iodine compatible. Examples of plastics that are iodine compatible and have low uptake are polypropylene and polystyrene. Plastics which have high uptake of iodine have unexpectedly been found to differ, significantly, in their release rate of iodine. An example of plastics that have high uptake and low release is copolyesters. Plastics which have high uptake and high release are styrene-ethylene-butylene-styrene copolymers. The mechanical properties of these various plastic materials do not significantly change with high iodine impregnation.

Due to the recognized variety of materials that respond differently to iodine impregnation, the present invention also provides a directional release material that controls the site and rate of iodine delivery. To this end, plastics of different compositions can be layered to create barriers for iodine release. Further, plastics can be impregnated with iodine at different times in the manufacturing process of useful products to confer an anti-microbial (bacteriocidal, virucidal, and fungicidal) property to the material.

Naturally, the selection of a suitable plastic material depends largely on the intended use of such material. For example, a particular plastic material may be selected because it has a fast halogen release rate, as opposed to another that has a slow halogen release rate. Among others, the following plastic materials may be utilized pursuant to the present invention: polyurethane; polypropylene; polystyrene; copolyester; polyethylene; polycarbonate/polyester blend and styrene-ethylene-butylene-styrene copolymer.

Because of the diversity of plastics and the potent activity of iodine as microbicidal agent, iodine impregnated plastics have a broad application for medical, industrial, food and water treatments. Examples of iodine impregnating materials that can be generated are: leukocyte filter pads; dialysis membranes; plastic beads to make a column for treating aqueous solutions; plastic balls used in water baths; blood bags; blood tubing; medical gloves; peritoneal dialysis catheters; and peritoneal dialysis connectors. Examples of materials to be disinfected with iodine impregnated plastics include: blood and its components including whole blood, red cell concentrates, plasma, platelet concentrates, plasma fractionation products including gamma globulin, coagulation products (e.g., Factor VIII, Factor IX, protein C, etc.), and albumin; recombinant products generated in tissue culture media; animal sera used in tissue culture media preparation (fetal calf, newborn calf, human sera); dairy products including milk; swimming pool water; industrial water (e.g. cooling tower water); sewage treatment water; tooth brush bristles; telephone handpieces; and bench tops.

By way of example, and not limitation, an experiment illustrating the impregnation of molecular iodine into a plastic material will now be given.

Experiment No. 1

This experiment determined the ability to impregnate polypropylene test tubes with iodine in various fluid vehicles. In addition, the experiment evaluated the ability of the impregnated test tubes to release iodine.

To impregnate polypropylene, 0.25 grams of elemental iodine (dark gray crystals) were placed in filter paper. The filter paper was then folded and taped shut so as to securely contain the iodine crystals. The filter paper containing the iodine was then placed in a 50 ml polypropylene centrifuge tube.

As the iodine gas was released from the solid phase iodine, it was taken up by the polypropylene. The color of polypropylene turned a light brown initially and progressively became a dark chocolate brown. A total of 24 tubes were treated in this manner. The tubes were allowed to incubate at room temperature for about two days. After the two days, the tubes were observed to be a uniform, dark chocolate brown color. This result indicated a substantial uptake of iodine had occurred. However, the iodine in one of the envelopes was opened and 0.2 grams of iodine could be recovered, demonstrating that a large amount of iodine was still present as solid crystals.

To demonstrate that iodine could be released by the iodine impregnated polypropylene tube, the following experiment was conducted using the preparations 1–3 below as extraction solutions.

(1) A saline solution (0.9% NaCl) was used. Iodine is known to be only slightly soluble in saline.

(2) A 10% solution of potassium iodide (KI) was used. Iodine is known to be highly soluble in aqueous solutions containing potassium iodide.

(3) A 200 mg/ml suspension of amylose in saline was used. The presence of elemental iodine can be detected using the characteristic color reaction of amylose going from a white material to a tan, violet and purple color in the presence of increasing concentrations of iodine.

The following steps were conducted to determine whether iodine could be recovered and also the rate of release of such iodine. Forty ml of an extraction solution (1–3 above) was added into separate iodine impregnated 50 ml polypropylene centrifuge tubes. The tubes were then placed on an end-over-end mixer. One ml samples were collected for all tubes after 45 minutes, 7.5 hours, 18 hours and 30 hours of rotation.

The following observations demonstrated that iodine could be recovered from the plastic and that the rate of release depends, among other factors, upon the solubility of iodine in the extraction media. First, only slight yellow discoloration of the saline solution was observed after 30 hours of rotation, indicating a slight amount of iodine was present in the saline. The potassium iodide solution The controls and samples were all then tested in Vero cells by a limiting dilution assay. The virus input, based on the untreated process control, was $10^{6.55}$ TCID 50/ml. Table 1 below details the assay results.

TABLE 1

| Sample | Virus Titer Input = $10^{6.55}$ TCID 50/ml | | | | Log Reduction | | | |
| --- | --- | --- | --- | --- | --- | --- | --- | --- |
| Bead Preparation | 0.5 hr. | 1 hr. | 2 hr. | 18 hr. | 0.5 hr. | 1 hr. | 2 hr. | 18 hr. |
| Bead Control | 7.25 | 7.08 | 4.28 | 5.33 | 0 | 0 | 2.27 | 1.22 |
| 0.25 g/ml | 4.63 | 1.83 | <1.83* | <1.83 | 1.92 | 4.72 | >4.72 | >4.72 |
| 0.1 g/ml | 6.55 | 6.20 | <1.83 | <1.83 | 0 | 0.35 | >4.72 | >4.72 |

\* = below the detection limit, no recoverable virus.

extracted out more iodine as indicated by a strong yellow color after 30 hours of rotation. The yellow color intensity was detectable after 45 minutes of rotation and became progressively stronger with time. This result demonstrated a sustained delivery of iodine into the solution. Still further, the amylose extraction solution became slightly discolored with yellow color after 45 minutes of incubation, violet/brown after 7 hours, dark purple after 8 hours and thereafter. This result demonstrates that elemental iodine was being released from the tubes into the saline media, and then captured by the amylose to produce the characteristic change in color of amylose caused by iodine.

By way of example, and not limitation, experiments illustrating the ability of the antimicrobial material of the present invention to inactivate viruses will now be given.

Experiment No. 2

This experiment determined the rate of vesicular stomatitis virus (VSV) inactivation by iodine impregnated polyurethane beads in tissue culture medium (RPMI 1640) at room temperature. The iodine impregnated polyurethane beads were prepared by incubating 100 grams of polyurethane pellets with 2 grams of crystal iodine at room temperature for 3–4 days.

TESTING PROCEDURE 30 ml of RPMI 1640 medium was placed into a 50 ml test tube. VSV (Indiana strain) was added to the media at 1/500 dilution.

Three (3) 50 ml test tubes were utilized for testing. 2.5 g of $I_2$-PU beads was added to the first test tube. 1 g of $I_2$-PU beads was added to the second test tube. 2.5 g of PU beads (PU bead control) was added to the third test tube. Each test tube was washed twice with 20 ml PBS each time. (Each gram of polyurethane beads contains about 30 pellets.)

10 ml of virus medium was added to each tube. The reaction incubation was carried out in end-over-end rotation at approximately 20 rpm speed. Untreated virus samples were collected as process control.

At 30 min, 1 hr, 2 hr and overnight (18 hr) intervals, one sample was collected from each group. The process control was collected at the 1 hr interval. The samples were quenched with 1.5% sodium thiosulfate to chemically neutralize iodine present in the sample.

Experiment No. 3

This experiment determined the rate of VSV inactivation by iodine impregnated polyurethane beads in normal human plasma at room temperature. The iodine impregnated polyurethane beads were prepared by incubating 100 grams of polyurethane pellets with 2 grams of crystal iodine at room temperature for 3–4 days.

TESTING PROCEDURE 40 ml of normal human plasma was placed into a 50 ml test tube. VSV (Indiana strain) was added to the media.

Three (3) 50 ml test tubes were utilized for testing. 2.5 g of $I_2$-PU beads was added to the first test tube. 1 g of $I_2$-PU beads was added to the second test tube. 2.5 g of PU beads (PU bead control) was added to the third test tube. Each test tube was washed twice with 20 ml PBS each time. (Each gram of polyurethane beads contains about 30 pellets.)

10 ml of virus plasma was added to each tube. The reaction incubation was carried out in end-over-end rotation at approximately 20 rpm speed. 2 ml of untreated virus plasma was placed in a sterile tube and was used as process control (no end-over-end rotation).

At 30 min, 1 hr, 2 hr and overnight (18 hr) intervals, one sample was collected from each group. The process control was collected at the 1 hr interval. The samples were quenched with 1.5% sodium thiosulfate to chemically neutralize iodine present in the sample.

The controls and samples were all then tested in Vero cells by a limiting dilution assay. The virus input, based on the untreated process control, was $10^{6.73}$ TCID 50/ml. Table 2 below details the assay results.

TABLE 2

| Sample | Virus Titer Input = $10^{6.73}$ TCID 50/ml | | | | | Log Reduction | | | | |
|---|---|---|---|---|---|---|---|---|---|---|
| Bead Preparation | 0.5 hr. | 1 hr. | 2 hr. | 4 hr. | 18 hr. | 0.5 hr. | 1 hr. | 2 hr. | 4 hr. | 18 hr. |
| Bead Control | 6.90 | 6.55 | 6.73 | 6.73 | 6.73 | 0 | 0.18 | 0 | 0 | 0 |
| 0.25 g/ml | 5.15 | 5.15 | 4.80 | 4.98 | 2.0 | 1.58 | 1.58 | 1.93 | 1.75 | 4.73 |
| 0.10 g/ml | 5.33 | 4.98 | 4.98 | 4.28 | 3.57 | 1.4 | 1.75 | 1.75 | 2.45 | 3.16 |

Experiment No. 4

This experiment determined the rate of HIV inactivation by iodine impregnated polyurethane beads in tissue culture medium (RPMI 1640) at room temperature. The iodine impregnated polyurethane beads were prepared by incubating 100 grams of polyurethane pellets with 2 grams of crystal iodine at room temperature for 3–4 days.

TESTING PROCEDURE 18 ml of RPMI 1640 medium was placed into a 50 ml test tube. HIV ($III_B$) was added to the media.

Nine (9) 15 ml test tubes were separated into three groups. To the first group, 0.5 g of $I_2$-PU beads was added to each test tube. 0.1 g of $I_2$-PU beads was added to each test tube in the second group. 0.5 g of PU beads (PU bead control) was added to each test tube in the third group. Each test tube was washed twice with 20 ml PBS each time. (Each gram of polyurethane beads contains about 30 pellets.)

2 ml of virus medium was added to each tube. The reaction incubation was carried out in end-over-end rotation at approximately 20 rpm speed. 2 ml of untreated virus medium was placed in a sterile tube and used as the process control.

At 1 hr, 2 hr and overnight (18 hr) intervals, one sample from each group was collected. The process control was collected at the 1 hr interval. The samples were quenched with 1.5% sodium thiosulfate to chemically neutralize iodine present in the sample.

The controls and samples were all then tested in MT-2 cells by a syncytial formation assay. This virus input, based on the untreated process control, was $10^{4.85}$ TCID 50/ml. Table 3 below details the assay results.

TABLE 3

| Sample | Virus Titer Input = $10^{4.85}$ TCID 50/ml | | | Log Reduction | | |
|---|---|---|---|---|---|---|
| Bead Preparation | 1 hr. | 2 hr. | 18 hr. | 1 hr. | 2 hr. | 18 hr. |
| Bead Control | 4.7 | 4.7 | 4.7 | 0.15 | 0.3 | 0 |
| 0.25 g/ml | <1.7* | <1.7* | <1.7* | >3.15 | >3.15 | >3.15 |
| 0.05 g/ml | 2.6 | <1.7* | <1.7* | 2.25 | >3.15 | >3.15 |

* = below detection limit, no recoverable virus.

Experiment No. 5

This experiment determined the rate of HIV inactivation by iodine impregnated polyurethane beads in 100% normal human plasma at room temperature. The iodine impregnated polyurethane beads were prepared by incubating 100 grams of polyurethane pellets with 2 grams of crystal iodine at room temperature for 3–4 days.

TESTING PROCEDURE 18 ml of normal human plasma was placed into a 50 ml test tube. HIV ($III_B$) was added to the media.

Nine (9) 15 ml test tubes were separated into three groups. To the first group, 0.5 g of $I_2$-PU beads was added to each test tube. 0.1 g of $I_2$-PU beads was added to each test tube in the second group. 0.5 g of PU beads (PU bead control) was added to each test tube in the third group. Each test tube was washed twice with 20 ml PBS each time. (Each gram of polyurethane beads contains about 30 pellets.)

2 ml of virus plasma was added to each tube. The reaction incubation was carried out in end-over-end rotation at approximately 20 rpm speed. 2 ml of untreated virus plasma was placed in a sterile tube and used as the process control.

At 1 hr, 2 hr and overnight (18 hr) intervals, one sample from each group was collected. The process control was collected at the 1 hr interval. The samples were quenched with 1.5% sodium thiosulfate to chemically neutralize iodine present in the sample.

The controls and samples were all then tested in MT-2 cells by a syncytial formation assay. The virus input, based on the untreated process control, was $10^{5.5}$ TCID 50/ml. Table 4 below details the assay results.

TABLE 4

| Sample | Virus Titer Input = $10^{5.5}$ TCID 50/ml | | | Log Reduction | | |
|---|---|---|---|---|---|---|
| Bead Preparation | 1 hr. | 2 hr. | 18 hr. | 1 hr. | 2 hr. | 18 hr. |
| Bead Control | 5.2 | 5.3 | 5.0 | 0.3 | 0.2 | 0.5 |
| 0.1 g/ml | 5.2 | 5.3 | 4.1 | 0.3 | 0.2 | 1.4 |
| 0.5 g/ml | <1.7* | <1.7* | <1.7* | >3.8 | >3.8 | >3.8 |

* = below detection limit, no recoverable virus.

By way of example, and not limitation, the results from experiments determining the differing absorption and release properties of various iodine impregnated plastics will now be given.

Various plastics were tested to determine their respective absorption and release properties with respect to iodine. For example, the following plastics were tested: polyurethane; polypropylene; polystyrene; copolyester; polyethylene; polycarbonate/polyester blend and styrene-ethylene-butylene-styrene copolymer.

Based on such testing, copolyesters (Hytrel™) and styrene-ethylene-butylene-styrene copolymers (Kraton™) were found to be the most effective plastic materials. The copolyesters used in the present invention are sold under the trademark Hytrel™ and may be obtained from DuPont located in Wilmington, Del. The styrene-ethylene-butylene-styrene copolymers used in the present invention are sold under the trademark Kraton™ and may be obtained from Shell located in Houston, Tex.

The description below focuses on the use of these particular plastic materials. However, the invention is not intended to be restricted to these materials, but extends to the breadth of the foregoing specification and the following claims. As one skilled in the art will appreciate, selection of a suitable plastic material depends largely on the use of such material. Therefore, the experimental results below simply provide illustrative details and should be understood to not restrict the present invention.

The absorption of iodine in plastics was first tracked by weight percentage. In various tests conducted, plastic samples were weighed before and after impregnation with iodine. Based on the difference in weight, the inventors were able to determine the amount of iodine absorbed into the plastic sample.

Based on the several studies that were initially evaluated, copolyesters (Hytrel™) and styrene-ethylene-butylene-styrene copolymers (Kraton™) both absorb high amounts of iodine. Continuous monitoring also showed that these two materials have different release rates. Styrene-ethylene-butylene-styrene copolymer quickly loses the iodine; copolyester retains iodine even under a well ventilated hood.

The next experiment determined the effect of iodine on the mechanical properties of various plastics. Iodine is an aggressive oxidative agent and readily attacks unsaturated polymers. Based on various tests, iodine was found to degrade polyisoprene, santoprene, silicone rubber, Ecdel, PCCE and even linear low density polyethylene (Insite CGCT).

Experiment No. 6

ABSORPTION TESTS

Figure 2:
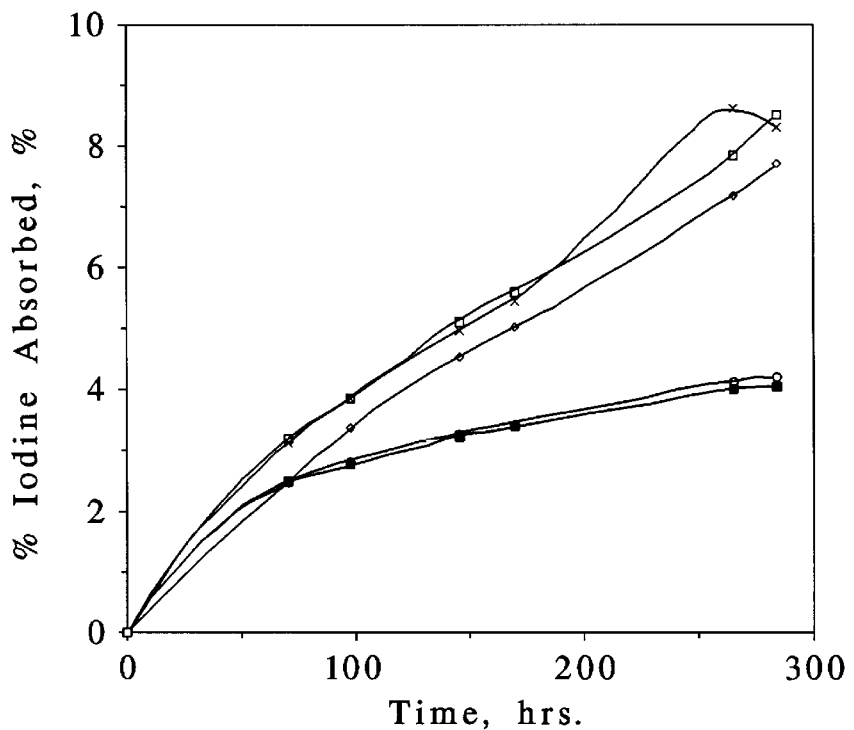
FIG. 2 illustrates the absorption rate by weight percent of various copolyesters and styrene-ethylene-butylene-styrene copolymers at room temperature.
Figure 3:
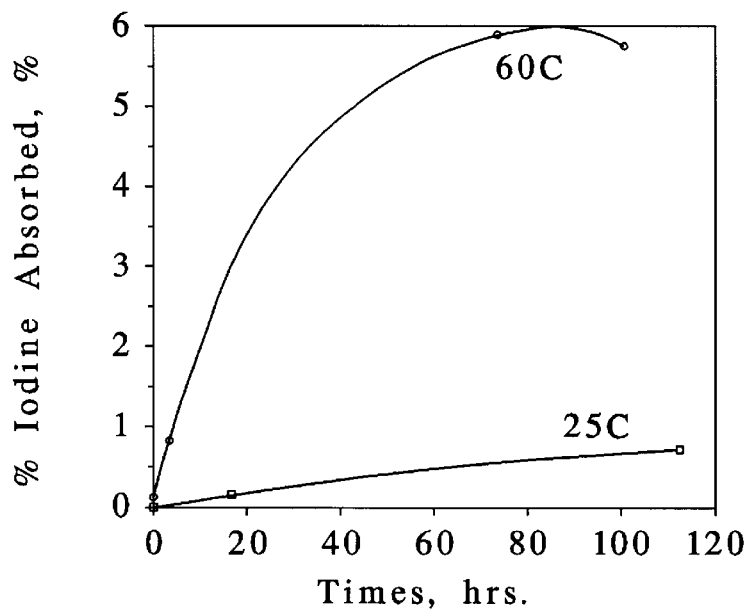
FIG. 3 illustrates the absorption rate by weight percent of a linear low density polyethylene at 60° C. and room temperature.

FIGS. 1–3 are illustrative absorption curves of different plastic materials. FIG. 1 is a graph of weight percent iodine absorbed versus time (hrs) samples of a linear, low density polyethylene (CGCT), a polypropylene (Escorene™), a copolyester (Hytrel™), a polycarbonate/polyester blend (Makroblend™), and a polystyrene. FIG. 2 is a graph of weight percent iodine absorbed versus time (day) for various copolyesters (Hytrel™) and styrene-ethylene-butylene-styrene copolymers (Kraton™) at room temperature. The copolyesters absorbed a greater percentage of iodine and are graphically represented on the upper portion of the graph. Whereas, the styrene-ethylene-butylene-styrene copolymers absorbed a lesser percentage of iodine and are graphically represented on the lower portion of the graph. Notably, the absorption rates for the various materials differ.

Certain factors may affect the absorption rates of these materials. Factors such as part geometry, iodine vessel container, iodine content and temperature may likely affect the absorption mechanism. As illustrated in FIG. 3, the effect of temperature is quite significant on the absorption rate. FIG. 3 shows the absorption rate by weight percentage versus time (hrs) of CGCT (LLDPE) at 60° C. and room temperature.

Experiment No. 7

IODINE RELEASE TESTS

After materials have been treated with iodine and removed from the absorption process, the iodine will slowly evaporate from the sample. This evaporation or release of iodine provides the anti-microbial action needed to keep components sterile. The rate of release is material dependent.

Figure 4:
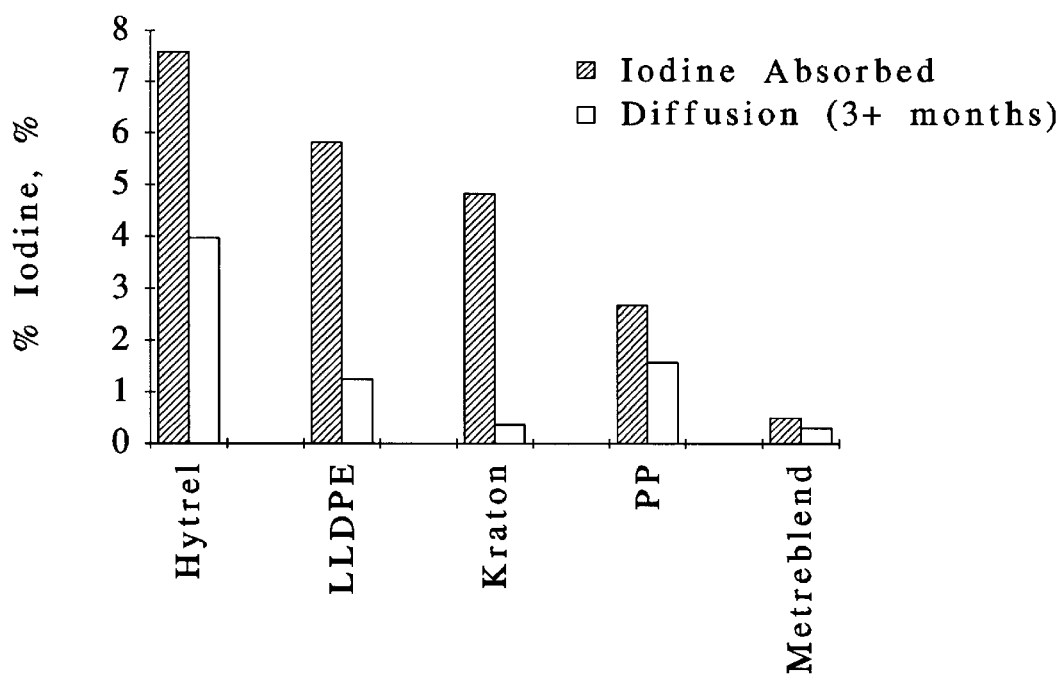
FIG. 4 illustrates the weight percentage of iodine absorbed and released from various plastic materials while placed under a lab hood.

FIG. 4 illustrates the release properties of various materials while placed under a lab hood.

Specifically, FIG. 4 illustrates the weight percentage of iodine absorbed and released from various materials over an extended period of time (i.e. three plus months).

The absorption levels indicated in FIG. 4 are not the maximum absorbency levels. However, the absorption levels give an indication of the release rates of different materials.

Figure 5:
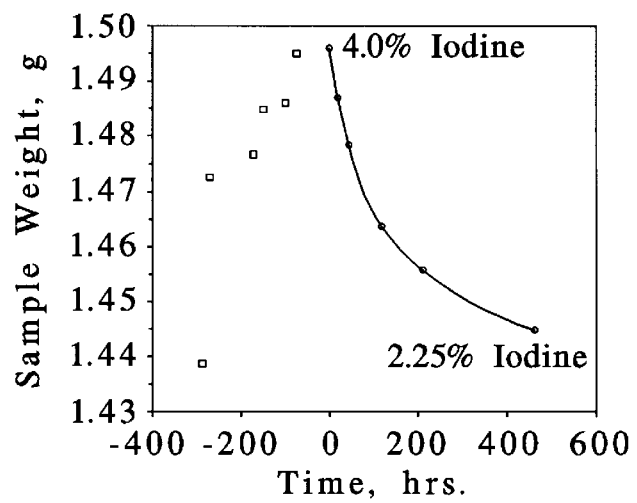
FIGS. 5 and 6 illustrate the short term release rates by weight (g) versus time (hrs) of styrene-ethylene-butylene-styrene copolymer and copolyester, respectively.
Figure 6:
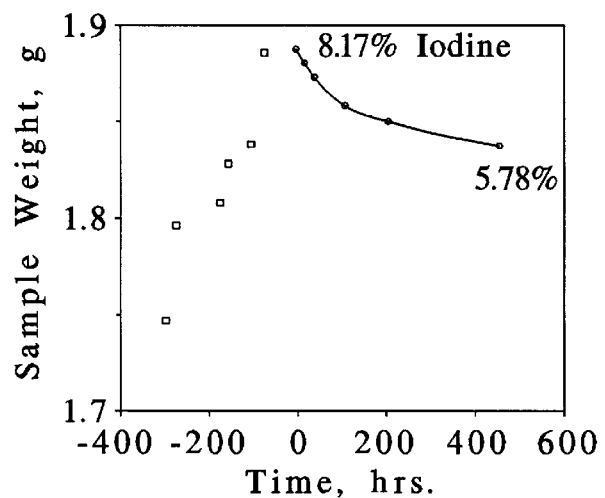

FIGS. 5 and 6 illustrate the short term release rates of styrene-ethylene-butylene-styrene copolymer and copolyester, respectively at 25° C. FIG. 6 illustrates how well the copolyester retains the absorbed iodine. Copolyester can retain at least 30% impregnated iodine after 6 months under a hood in an open vial.

Experiment No. 8

MECHANICAL PROPERTIES

The effect of iodine on the mechanical properties of several polymers has also been studied. Experiments were conducted to evaluate whether iodine adversely affected the utility and performance of the impregnated plastic material for industrial and medical uses. While iodine can readily degrade some polymers, others seem relatively unaffected. The following information details the experiments conducted to test the mechanical stability of the various treated plastics. Various plastics were tested in both an open as well as a closed type system.

Preparation:

Samples, injection molded tensile bars, were placed in conical flasks sealed by glass stoppers. The iodine was weighed, at least 2 g, and packaged in filter paper pouches. The pouches were then placed in the glass containers. In order to accelerate the absorption, some samples were placed in an oven at 60° C.

Open System vs. Closed System:

In order to survive the shelf and service life, it is desirable for the impregnated materials to be shrouded to minimize iodine diffusion. The open system represents the service life of the material after the product has been opened. The closed system represents the effect of iodine during the shelf life of the product. Testing within a closed system is expected to be more severe on the mechanical properties since the iodine content remains high throughout the testing period.

Tables 5A–6B set forth the resulting effects of iodine impregnation on the mechanical properties of the various plastics. The testing evaluates the effect of not only the storage conditions, eg. open system, but also the iodine content, temperature of impregnation, and the exposure period. For each plastic sample, the tensile strength and the elongation percentage were also determined.

Tables 5A and 5B illustrate mechanical testing conducted in an open system with a temperature of impregnation of 60° C. As these tables illustrate, Hytrel™ samples absorbed for 3 days to 8% iodine show no significant effect after 4 months. Whereas, Hytrel™ samples absorbed for 5 days to 14% iodine became immediately brittle. Kraton™ samples absorbed for 3 days to 5% iodine show no significant effect after 4 months. Polypropylene samples absorbed for 12 days to 2.6% iodine show a 30% decrease in percent elongation at break. Still further, linear low density polyethylene (LLDPE) samples absorbed for 12 days to 4.56% iodine show a 35% decrease in percent elongation at break.

TABLE 5A

| Material | Original Iodine Content % | Time to Test | Iodine content at test (%) | Tensile strength, PSI | Std. Dev. |
|---|---|---|---|---|---|
| Kraton G 2705 | Control | — | — | 817.5 | 14.85 |
|  | 4.2 | 2 weeks | 0.35 | 901 | 63.69 |
|  | 7.99 | 2 weeks | 0.66 | 944.33 | 51.64 |
|  | 4.86 | 4 months | 0.8 | 895.75 | 44.7 |
|  | 4.2 | 4 months | 0.27 | 910.6 | 19.73 |
| Polystyrene | Control | — | — | 7163.44 | 30.8 |
|  | 4.21 | 4 months | 1 | 6152.5 | 356.13 |
| Hytrel 4056 | Control | — | — | 4264.5 | 323.15 |
|  | 7.55 | 2 weeks | 4 | 4315 | 82.02 |
|  | 14.27 | 2 weeks | 11 | 1406.33 | 68.84 |
|  | 7.55 | 4 months | 3.88 | 4143.5 | 135.57 |
| CGCT (LLDPE) | Control | — | — | 2730.5 | 54.45 |
|  | 4.56 | 2 weeks | 4 | 2303 | 48.08 |
| Escorene PD9214 (PP) | Control | — | — | 5257.5 | 142.13 |
|  | 1.4 | 4 months | 0.9 | 5492.4 | 57.87 |
|  | 2.6 | 4 months | 1.5 | 5649.9 | 24.82 |

TABLE 5B

| Material | Original Iodine Content % | Time to Test | Iodine content at test (%) | Elongation % | Std. Dev. |
|---|---|---|---|---|---|
| Kraton G 2705 | Control | — | — | 179.95 | 21.43 |
|  | 4.2 | 2 weeks | 0.35 | 211.83 | 45.83 |
|  | 7.99 | 2 weeks | 0.66 | 167.53 | 23.05 |
|  | 4.86 | 4 months | 0.8 | 206.53 | 34.88 |
|  | 4.2 | 4 months | 0.27 | 194.8 | 17.67 |
| Polystyrene | Control | — | — | 13.28 | 0.88 |
|  | 4.21 | 4 months | 1 | 5.64 | 0.54 |
| Hytrel 4056 | Control | — | — | 268.55 | 30.19 |
|  | 7.55 | 2 weeks | 4 | 314.7 | 6.65 |
|  | 14.27 | 2 weeks | 11 | 11.46 | 0.21 |
|  | 7.55 | 4 months | 3.88 | 316.4 | 24.58 |
| CGCT (LLDPE) | Control | — | — | 376.85 | 2.33 |
|  | 4.56 | 2 weeks | 4 | 251 | 3.68 |
| Escorene PD9214 (PP) | Control | — | — | 46.75 | 1.48 |
|  | 1.4 | 4 months | 0.9 | 41.82 | 3.03 |
|  | 2.6 | 4 months | 1.5 | 34.33 | 3.64 |

Tables 6A and 6B illustrate mechanical testing conducted in an closed system with a temperature of impregnation of 25° C. Under such a closed system, Hytrel™ samples absorbed to 4.3% iodine did not show any effect after six days. Isoplast polyurethane (PU) samples absorbed to 0.08% iodine did not show any significant effect after nine weeks. In contrast, Prevail polyurethane samples absorbed to 14% iodine become brittle after nine weeks. Whereas, Pellethane polyurethane samples absorbed to 4.6% iodine did not show any significant effect.

TABLE 6A

| Material | Iodine Content (%) | Time to Test | Tensile strength, PSI | Std. Dev. |
|---|---|---|---|---|
| Hytrel 5555HS | Control | — | 4737.28 | 268.21 |
|  | 1.14 | 3 days | 4486 | 335.93 |
|  | 4.27 | 6 days | 4685.22 | 438.98 |
| Isoplast 2510 (PU) | Control | — | 8505.8 | 139.56 |
|  | 0.08 | 4 weeks | 8472.33 | 6897 |
|  | 0.08 | 9 weeks | 8315 | 0 |
| LDPE | Control | — | 1539.2 | 23.26 |
|  | 0.6 | 3 weeks | 1516 | 22.63 |
| Prevail 3150 (PU) | Control | — | 3904.5 | 12.02 |
|  | 14 | 9 weeks | 3484.5 | 68.59 |
| Pellethane (PU) | Control | — | 6061.32 | 296.18 |
|  | 1.85 | 10 days | 5595.9 | 182.93 |
|  | 4.6 | 1 month | 5591.81 | 199.99 |
| PP/Kraton blend 70% Escorene PD9214 30% Kraton G2705 | Control | — | 3507.46 | 55.47 |
|  | 1 | 10 days | 4486 | 150.35 |
|  | 4.27 | 1 month | 4685.22 | 438.98 |
| PP/Kraton blend 50% Escorene PD9214 50% Kraton G2705 PP/Kraton blend | Control | — | 2443.01 |  |
|  | 1.7 | 10 days | 2600.7 | 119.36 |
|  | 2.6 | 1 month | 2689.28 | 36.58 |
| 30% Escorene PD9214 | Control | — | 1659.14 | 67.8 |

TABLE 6A-continued

| Material | Iodine Content (%) | Time to Test | Tensile strength, PSI | Std. Dev. |
|---|---|---|---|---|
| 70% Kraton G2705 | 2.2 | 10 days | 1668.48 | 71.5 |
|  | 3.2 | 1 month | 1748.48 | — |

TABLE 6B

| Material | Iodine Content (%) | Time to Test | % Elongation, % | Std. Dev. |
|---|---|---|---|---|
| Hytrel 5555HS | Control | — | 335 | 20.811 |
|  | 1.14 | 3 days | 150.35 | 18.64 |
|  | 4.27 | 6 days | 351.5 | 50.2 |
| Isoplast 2510 PU | Control | — | 127.89 | 47.15 |
|  | 0.08 | 4 weeks | 154.37 | 35.1 |
|  | 0.08 | 9 weeks | 98.9 | 30.12 |
| LDPE | Control | — | 108.48 | 12.26 |
|  | 0.6 | 3 weeks | 137.5 | 93.34 |
| Prevail 3150 PU | Control | — | 90.6 | 1.23 |
|  | 14 | 9 weeks | 5.2 | 0.99 |
| Pellethane TPU | Control | — | 258.98 | 8.96 |
|  | 1.85 | 10 days | 269.32 | 11.96 |
|  | 4.6 | 1 month | 251.2 | 18.18 |
| PP/Kraton blend |  |  |  |  |
| 70% Escorene PD9214 | Control | — | 372.44 | 16.23 |
| 30% G2705 | 1 | 10 days | 335.93 | 18.64 |
|  | 4.27 | 1 month | 351.5 | 50.2 |
| PP/Kraton blend 50% Escorene PD9214 | Control 1.7 | 10 days | 308.48 | 39.85 |
| 50% G2705 PD/Kraton blend | 2.6 | 1 month | 325.3 | 10.45 |
| 30% Escorene PD9214 | Control | — | 248.98 | 29.94 |
| 70% G2705 | 2.2 | 10 days | 232.45 | 4.45 |
|  | 3.2 | 1 month | 201.34 | — |

Tables 5A–6B illustrate that impregnating iodine into various polymeric materials does not adversely effect the mechanical properties of the various polymeric materials. While mechanical properties and dimensions changed after impregnation, they were still acceptable. As a result thereof, various polymeric materials can be impregnated with iodine and still be utilized to produce, for example, medical and industrial apparatuses.

Impregnation Results:

This experiment presents results from a impregnation feasibility examination. The following materials or blends were chosen for the iodine impregnation study: (1) copolyester; (2) polyurethane; (3) styrene-ethylene-butylene-styrene copolymer; (4) PVP/copolyester; and (5) PVOH/styrene-ethylene-butylene-styrene copolymer.

Disks and mini tensile bars were cut from a compression molded sheet. Iodine impregnation was done in a vacuum (−15 to −25 psi) oven with a temperature of 116 +/−3° F. for about 24 hours. Samples were first kept in a closed vial and then placed in the vacuum oven.

Figure 7:
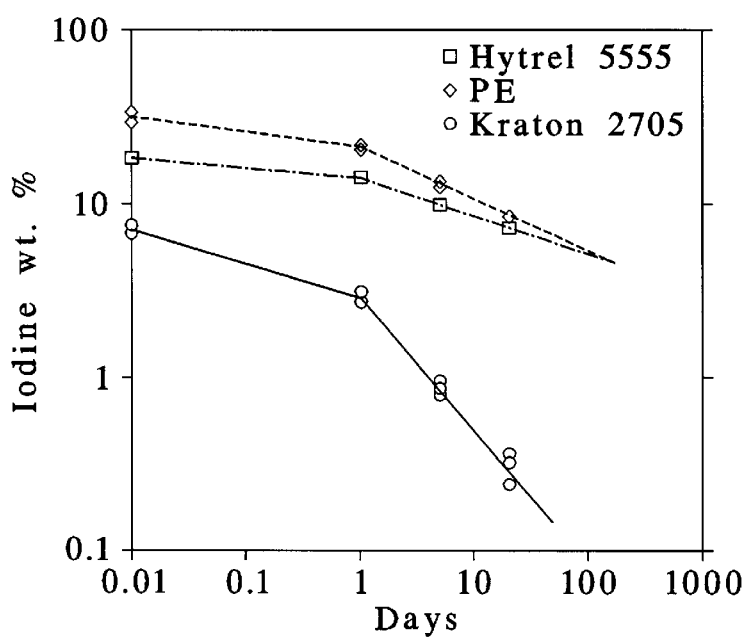
FIG. 7 illustrates the iodine release rate in weight percent versus days for three plastic materials tested in the present invention.

After iodine treatment, the following three parameters were monitored for a period of two months: (1) iodine weight loss; (2) mechanical properties; and (3) dimension. FIG. 7 illustrates the iodine release rate for three polymeric materials while under a vented hood. Tables 7A, 7B and 7C set forth the percentage weight loss data collected over the two month study period. FIGS. 8–10 illustrate the effects of iodine on the elongation of a copolyester, a polyurethane, and a styrene-ethylene-butylene-styrene copolymer, respectively. Likewise, table 8 sets forth the mechanical elongation data collected over the two month period.

TABLE 7A

| Sample ID | Material | % Iodine | % Thickness Change 0 day | % Thickness Change 19 days |
|---|---|---|---|---|
| 98-1 | Hytrel | 15.65 | 3.47 | 1.93 |
| 98-2 | Hytrel | 15.86 | 0.88 | 1.75 |
| 98-3 | Hytrel | 18.74 | 1.72 |  |
| 98-4 | Hytrel | 18.89 | 2.15 | 1.29 |
| 98-5 | Hytrel | 17.8 | 1.27 | 0.42 |
| 98-8 | Hytrel | 18.07 | 1.68 | 0.84 |
| 98-7 | PU | 34.03 | 0.81 | 0.81 |
| 98-8 | PU | 28.13 | 2.49 | 0.36 |
| 98-9 | PU | 32.23 | 1.61 | 0 |
| 98-10 | PU | 30.05 | 1.54 | 0 |
| 98-11 | PU | 32.57 | 0 | −0.81 |
| 98-12 | PU | 28.1 | 3.7 | 0 |
| 98-13 | Kraton | 6.5 | 0 | −1.37 |
| 98-14 | Kraton | 6.6 | 0 | −0.68 |
| 98-15 | Kraton | 7.27 | 0 | 1.35 |
| 98-16 | Kraton | 7.38 | 0 | 0 |
| 98-17 | Kraton | 6.69 | −0.69 | 0 |
| 98-18 | Kraton | 7.37 | −1.35 | 0 |

TABLE 7B

| Sample ID | Material | Dissipation System | % Iodine Day 1 | % Iodine Day 5 |
|---|---|---|---|---|
| 98-1 | Hytrel | Close | 15.32 |  |
| 98-2 | Hytrel | Close |  |  |
| 98-3 | Hytrel | Close |  |  |
| 98-4 | Hytrel | Open | 14.23 | 10.27 |
| 98-5 | Hytrel | Open | 13.75 | 10.19 |
| 98-6 | Hytrel | Open | 14.15 | 10.25 |
| 98-7 | PU | Close |  |  |
| 98-8 | PU | Close |  |  |
| 98-9 | PU | Close |  |  |
| 98-10 | PU | Open | 21.91 | 13.45 |
| 98-11 | PU | Open | 22.32 | 13.80 |
| 98-12 | PU | Open | 20.71 | 12.38 |
| 98-13 | Kraton | Close |  |  |
| 98-14 | Kraton | Close |  |  |
| 98-15 | Kraton | Close |  |  |
| 98-16 | Kraton | Open | 3.04 | 0.92 |
| 98-17 | Kraton | Open | 2.73 | 0.76 |
| 98-18 | Kraton | Open | 3.11 | 0.84 |

TABLE 7C

| Sample ID | Material | % Iodine Day 19 | % Iodine 54 Days | Average |
|---|---|---|---|---|
| 98-1 | Hytrel | 15.18 | 15.03 | ~15%(closed) |
| 98-2 | Hytrel | 15.44 | 15.45 | " |
| 98-3 | Hytrel | 9.12* | 9.20 |  |
| 98-4 | Hytrel | 7.58 | 6.31 | 6.24 ± 0.07%(open) |
| 98-5 | Hytrel | 7.49 | 6.18 | " |
| 98-6 | Hytrel | 7.54 | 6.24 | " |
| 98-7 | PU | 26.6* | 22.03 | ~23%(closed) |
| 98-8 | PU | 23.78 | 22.06 | " |
| 98-9 | PU | 27.45 | 24.06 | " |
| 98-10 | PU | 8.73 | 5.28 | 4.97% ± 0.53(open) |
| 98-11 | PU | 8.91 | 5.26 | " |
| 98-12 | PU | 7.59 | 4.36 | " |
| 98-13 | Kraton | 5.59 | 5.36 | 5.57 ± 0.3(closed) |
| 98-14 | Kraton | 5.41 | 5.43 | " |
| 98-15 | Kraton | 6.08 | 5.91 | " |
| 98-16 | Kraton | 0.38# | 0.19 | 0.20 ± 0.04(open) |

TABLE 7C-continued

| Sample ID | Material | % Iodine Day 19 | % Iodine 54 Days | Average |
|---|---|---|---|---|
| 98-17 | Kraton | 0.24# | 0.17 | " |
| 98-18 | Kraton | 0.33# | 0.25 | " |

*Leak, aluminum rusted
Color back to clear (almost)

TABLE 8A

| Sample ID | Material | % Iodine |
|---|---|---|
| 89-1T | PVOH/Kraton | 37.4 |
| 89-2T | Hytrel | 20.6 |
| 89-3T | PE192 | N/A |
| 89-4T | Kraton | 6.7 |
| 89-5T | PVP/Hytrel | 13.02 |
| 95-2 | PE192 | 11.60 |
| 93-1 | PU | 0.83 |
| 93-2 | PVOH/Kraton | 0.66 |
| 93-3 | PVP/Hytrel | 0.87 |
| 98-4 | Hytrel | 0.73 |
| 98-5 | Kraton | 0.66 |

TABLE 8B

| Sample ID | Material | % Elongation w/o Iodine | 0th mon | 1th mon | 2nd mon |
|---|---|---|---|---|---|
| 89-1T | PVOH/Kraton | 1300 | 700 | 659 | — |
| 89-2T | Hytrel | 784 | 800 | 448 | 468(n = 4) |
| 89-3T | PE192 | — | — | — | — |
| 89-4T | Kraton | 1077 | 688 | 624 | 570(n = 2) |
| 89-5T | PVP/Hytrel | 1000 | 44 | 12 | — |
| 95-2 | PE192 | >1000 | | 294 | 212(n = 2) |
| 93-1 | PU | | | 835 | 994 |
| 93-2 | PVOH/Kraton | | | >1000 | — |
| 93-3 | PVP/Hytrel | | | 847 | — |
| 98-4 | Hytrel | | | 0 | — |
| 98-5 | Kraton | | | >1000 | >1000 |

Based on the multitude of tests conducted, copolyester and styrene-ethylene-butylene-styrene copolymer proved to be the most effective materials. Table 9 below details the key properties of these materials as well as those of polyurethane.

TABLE 9

| Material | Flexibility | % iodine capacity | Dissipation 0,2 6 months open system | seal | elongation retention 0, 1, 2 months | | |
|---|---|---|---|---|---|---|---|
| Kraton-2705 | Very flexible | 7% | 7% 0.2% <0.1% | excellent | 100% | 56% | 58% |
| Hytrel-5555 | semi-flexible | >20% | 18% 6.2% >2% | poor-fair | 64% | 58% | 53% |
| Polyurethane | flexible | >30% | 30% 5% >2% | Good | | | |
| Polyurethane | | | | | 100% | 20% | 20% |

By way of example, and not limitation, test results illustrating the microbicidal activity of the present invention will now be given.

Experiment No. 9

MICROBICIDAL RESULTS

This experiment presents results from a microbiology feasibility examination. The tests were performed on a range of plastic materials, varying concentrations of iodine, and several impregnation process parameters.

The test methods chosen were based on the requirement that any antimicrobial intended for use on the external areas of a certain medical device, namely continuous ambulatory peritoneal dialysis (CAPD) connectors, have the role of preventing bioburden accumulation. For example, accidental contamination of the connector external areas during an exchange should be eliminated within the dwell time period to prevent bioborder accumulation.

The initial testing of materials consisted of the following test parameters: 1) direct surface contamination; 2) *Staphylococcus aureus* as the contaminating organism at a level of $10^5$ colony forming units; and 3) exposure time of 15 minutes.

These initial parameters were chosen for the following reasons. The initial concept was to use an antimicrobial substance on areas prone to touch contamination. *Staphylococcus aureus* is the second most prevalent cause of CAPD peritonitis. It was chosen because it is comparable to *S. epidermidis* in sensitivity to iodine but is less likely to be an extraneous contaminant that may result in false test failures. A five $\log_{10}$ reduction of viable contaminants was chosen to represent worst case touch or airborne contamination. Published literature and previous work show that povidone iodine can effectively disinfect surfaces in a fairly short exposure time (less that 10 min).

The test parameters for subsequent testing was modified slightly. First, the testing examined those scenarios where the impregnated material is not directly exposed to touch contamination but contacts other surfaces that may be exposed. To adequately evaluate this scenario, non-impregnated materials were contaminated and then impregnated materials were placed on top of a "sandwich" configuration. Second, the exposure time was lengthened to one hour. Realistically, the CAPD dwell period is approximately four hours; testing one hour instead of 15 minutes still gives a large safety factor.

Tables 10A and 10B display the various materials evaluated for antimicrobial effectiveness. Copolyesters (Hytrel™) and styrene-ethylene-butylene-styrene copolymers (Kraton™) materials were most extensively studied. These materials impregnated with even very low levels of iodine (approx. 1%) were effective. Copolyester samples with an original iodine concentration of 7.55% were still effective after 4 months of storage in a container open to the atmosphere. Both copolyester and styrene-ethylene-butylene-styrene copolymer samples with original iodine concentrations of 1.25% and 1.21% respectively were effective after 6 weeks storage in a closed container.

TABLE 10A

| Material | Original Iodine Content(%) | Temp. of Impregnation (C.) | Storage Condition | Time to Test |
|---|---|---|---|---|
| Hytrel 4056 | 5.5 | 25 | Closed | 0 |
| Hytrel 4056 | 1.3 | 60 | Closed | 0 |
| Hytrel 4056 | 0.5 | 60 | Closed | 0 |
| Hytrel 4056 | 7.55 | 60 | Open | 20 dys |
| Hytrel 5555 | 10.0 | 25 | Closed | 2 wks |
| Hytrel 5555 | 17.26 | 47(vacuum) | Closed | 2 wks |
| Hytrel 5555 | 17.26 | 47(vacuum) | Closed | 5 wks |
| Hytrel 5555 | 6.73 | 25 | Closed | 6 wks |
| Hytrel 4056 | 7.55 | 60 | Open | 4 mos |
| Hytrel 5555 | 1.23 | 47(vacuum) | Closed | 6 wks |
| Kraton 2705 | 3.4 | 25 | Closed | 0 |
| Kraton 2705 | 3.4 | 25 | Closed | 2 mos |
| Kraton 2705 | 3.4 | 25 | Closed | 4 mos |
| Kraton 2705 | 3.4 | 25 | Closed | 4 mos |
| Kraton 2705 | 0.3 | 60 | Closed | 0 |
| Kraton 2705 | 0.788 | 60 | Closed | 0 |
| Kraton 2705 | 5.0 | 60 | Open | 2 wks |
| Kraton 2705 | 1.0 | 60 | Open | 2 mos |
| Kraton 2705 | 4.8 | 60 | Open | 2 wks |
| Kraton 2705 | 4.8 | 60 | Open | 10 wks |
| Kraton 2705 | 4.8 | 60 | Open | 10 wks |
| Kraton 2705 | 2.5 | 25 | Closed | 1 mo |
| Kraton 2705 | 2.95 | 47(vacuum) | Closed | 2 wks |
| Kraton 2705 | 2.95 | 47(vacuum) | Closed | 5 wks |
| Kraton 2705 | 2.54 | 25 | Closed | 6 wks |
| Kraton 2705 | 1.21 | 47(vacuum) | Closed | 6 wks |
| Kraton 2705 | 4.9 | 47(vacuum) | Closed | 4 wks |
| CGCT (LLDPE) | 1 | 60 | Open | 1 mo |
| CGCT (LLDPE) | 5.8 | 60 | Open | 42 dys |
| CGCT (LLDPE) | 5.8 | 60 | Open | 4 mos |
| Escorene (PP) | 1.4 | 60 | Open | 2 wks |
| 50% PP/50% Kraton | 1.7 | 25 | Closed | 2 wks |
| 70% PP/30% Kraton | 1.0 | 25 | Closed | 2 wks |
| PE 192 | 18.85 | 47(vacuum) | Closed | 2 wks |
| PE 192 | 18.85 | 47(vacuum) | Closed | 5 wks |

*ND = not determined

TABLE 10B

| Material | Iodine Content at Test (%) | Test Method | 5$\log_{10}$ reduction of SA (Y/N) |
|---|---|---|---|
| Hytrel 4056 | Same | Surface 15 min | Y |
| Hytrel 4056 | Same | Surface 15 min | Y |
| Hytrel 4056 | Same | Surface 15 min | Y |
| Hytrel 4056 | 4.1 | Surface 15 min | Y |
| Hytrel 5555 | ND* | Sandwich 15 min | Y |
| Hytrel 5555 | ND | Sandwich 15 min | Y |
| Hytrel 5555 | ND | Sandwich 60 min | Y |
| Hytrel 5555 | ND | Sandwich 60 min | Y |
| Hytrel 4056 | 3.9 | Sandwich 60 min | Y |
| Hytrel 5555 | ND | Sandwich 60 min | Y |
| Kraton 2705 | Same | Surface 15 min | Y |
| Kraton 2705 | 0.625 | Surface 15 min | Y |
| Kraton 2705 | ND | Surf + Oil 15 min | Y |
| Kraton 2705 | ND | Surf/no oil 15 min | Y |
| Kraton 2705 | Same | Surface 15 min | Y |
| Kraton 2705 | Same | Surface 15 min | Y |
| Kraton 2705 | 0.48 | Surface 15 min | N (1$\log_{10}$ reduc) |
| Kraton 2705 | 0.88 | Surface 15 min | Y |
| Kraton 2705 | 0.9 | Surface 15 min | N (1$\log_{10}$ reduc) |
| Kraton 2705 | ND | Surf + Oil 15 min | N (.9$\log_{10}$ reduc) |
| Kraton 2705 | ND | Surf/no oil 15 min | N (2$\log_{10}$ reduc) |
| Kraton 2705 | ND | Sandwich 15 min | Y |
| Kraton 2705 | ND | Sandwich 15 min | Y |
| Kraton 2705 | ND | Sandwich 60 min | Y |
| Kraton 2705 | ND | Sandwich 60 min | Y |
| Kraton 2705 | ND | Sandwich 60 min | Y |
| CGCT (LLDPE) | 0.26 | Surface 15 min | N (.2$\log_{10}$ reduc) |
| CGCT (LLDPE) | 1.78 | Surface 15 min | N (1.5$\log_{10}$ reduc) |
| CGCT (LLDPE) | 1.19 | Sandwich 15 min | Y |
| Escorene (PP) | 1.4 | Surface 15 min | N (.6$\log_{10}$ reduc) |
| 50%PP/50% Kraton | ND | Sandwich 15 min | Y |
| 70%PP/30% Kraton | ND | Sandwich 15 min | Y |
| PE 192 | ND | Sandwich 15 min | Y |
| PE 192 | ND | Sandwich 60 min | Y |

*ND = not determined

A few samples of polypropylene-kraton blends and polyurethane also showed effectiveness. The two materials that did not show consistent 5 $\log_{10}$ reduction of *S. aureus* were linear low density polyethylene (CGCT) and polypropylene (Escorene™).

In addition to the above test parameters, preliminary testing on the effects of glycerol (simulating body oil) on antibacterial activity as well as the effect of temperature was evaluated. An evaluation of the effects of glycerol on antibacterial activity of impregnated material showed that oils can reduce the effectiveness. However, reduction of effectiveness is not observed when the iodine level is high, presumably in excess of the necessary bactericidal concentration. The inventors believe that the temperature used in the iodine impregnation process may impact either effectiveness and/or longevity.

The present invention also provides a method for making an antimicrobial material. The method includes the step of contacting a plastic material with a halogen gas that is thereby absorbed in the plastic material.

As set forth above, iodine impregnated plastics have a broad application for medical, industrial, food and water treatments. In an embodiment, the plastic material may be formed into a medical apparatus prior to contacting same with the halogen gas.

Likewise, the present invention provides a method for impregnating a plastic material. Pursuant to this method, iodine crystals are initially delivered in an enclosed vessel. Then, the plastic material to be impregnated is placed in the enclosed vessel for a time sufficient to allow the iodine to absorb into the plastic material.

By way of example, and not limitation, different conceptual methods of impregnating iodine into a plastic material pursuant to the present invention will now be given. While the following examples focus on the impregnation of a dialysis connector for use in a dialysis system, the present invention is not intended to be limited by these examples.

Concept 1

Iodine Impregnated Cap

Figure 11:
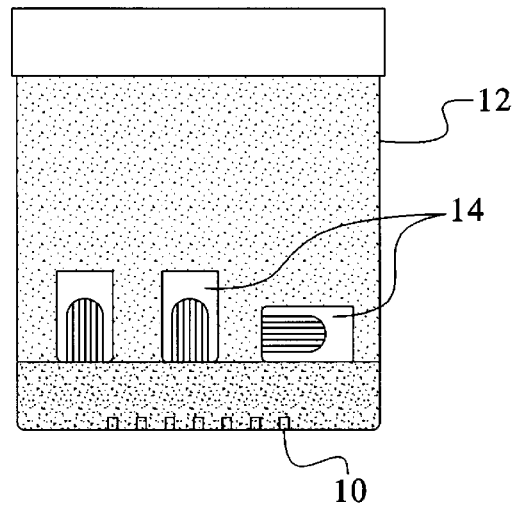
FIG. 11 illustrates a method of impregnating plastic samples pursuant to the present invention.

As illustrated in FIG. 11, exposing plastic caps 14 to elemental iodine in an enclosed vessel 12 impregnates the caps 14 with iodine. Initially, a source of gaseous iodine 10, such as dry iodine crystals, is placed in an enclosed vessel 12. Then, plastic caps 14 are placed in the enclosed vessel 12 for a time sufficient to allow the iodine to absorb into the plastic caps 14. Effectively, the elemental iodine sublimes into the enclosed vessel 12 and then absorbs into the plastic caps 14.

Figure 12:
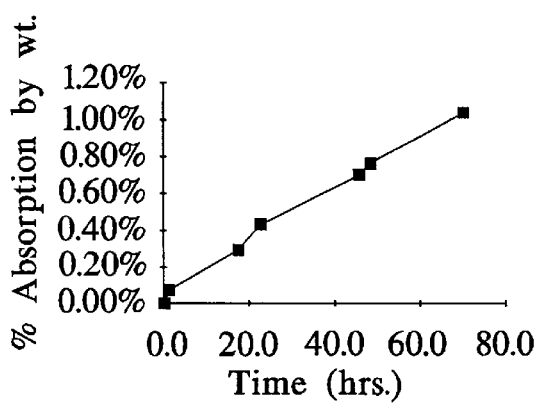
FIG. 12 illustrates the absorption of iodine by weight percentage versus time into copolyester samples.
Figure 13:
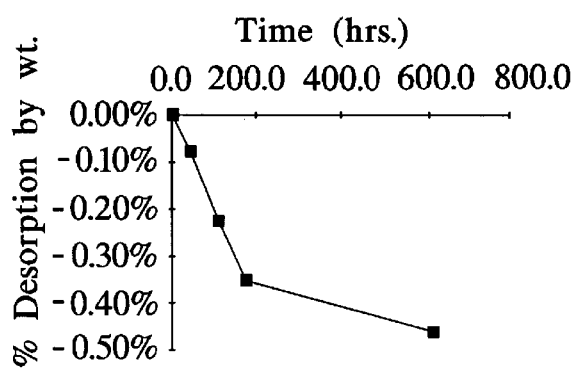
FIG. 13 illustrates the release rate of iodine by weight percentage versus time for copolyester samples.

The iodine is absorbed into the plastic caps 14 over time at a rate that is dependent on temperature, the amount of iodine in the vessel 12, and the type of plastic. FIG. 12 illustrates iodine absorption by weight percentage versus time into Hytrel® caps at 25° C. Release of iodine from the cap occurs when the cap is removed from the iodine source and open to the atmosphere. The rate of iodine release is dependent on iodine concentration in the plastic, temperature and the type of plastic. FIG. 13 shows the iodine release rate by weight percentage versus time for Hytrel® caps at 25° C.

Antimicrobial testing conducted on samples produced in this manner exhibited a 5 $\log_{10}$ reduction of *S. aureus* at iodine concentrations as low as 0.43%. This test proved preliminary feasibility of this conceptual method.

Figure 14:
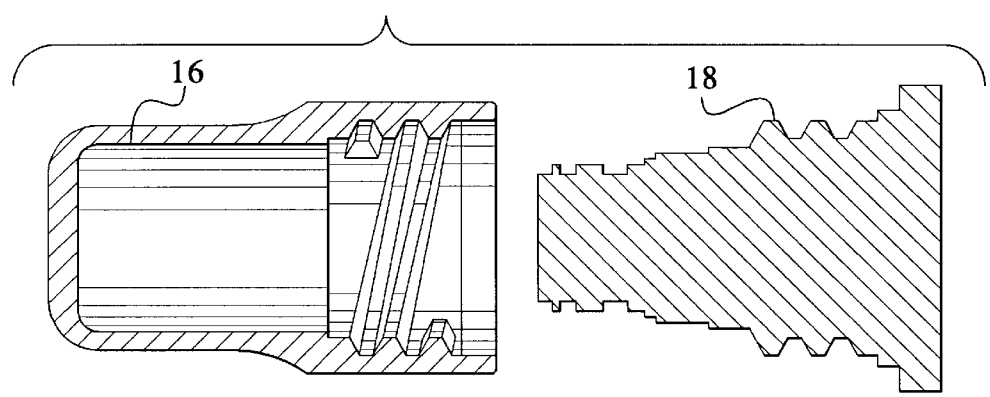
FIG. 14 illustrates an iodine impregnated dialysis cap with a corresponding dialysis connector.

In an embodiment, as illustrated in FIG. 14, a disconnect cap 16 for peritoneal dialysis can be impregnated with iodine. The iodine is slowly released from the disconnect cap 16 and disinfects the dialysis connector 18 upon insertion of the connector 18 into the cap 16.

Concept 2

Pre-impregnated Disk in a Cap

For most applications, blocking iodine release from unwanted areas, such as onto the user's fingers or clothing, and concentrating the released iodine at the disinfection site is desirable. For example, releasing iodine from the inside of a cap and not the outside would be beneficial.

Figure 15:
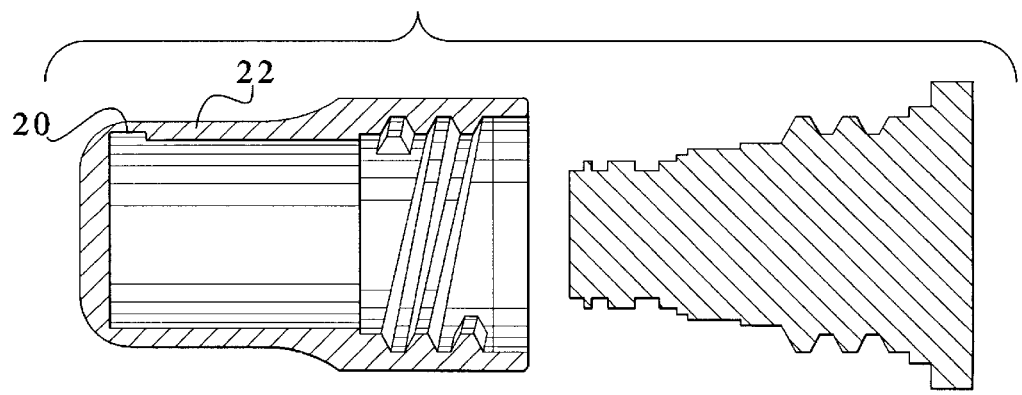
FIG. 15 illustrates a dialysis cap including an impregnated disk with a corresponding dialysis connector.

In this concept, a plastic disk is impregnated with iodine by the same method that the cap is impregnated in Concept 1. As illustrated in FIG. 15, after the disk 20 is impregnated, the disk 20 is placed inside the bottom of an iodine resistant cap 22 and sealed inside an iodine barrier package. The disk 20 contains the iodine and the cap 22 serves as a barrier to prevent the iodine from escaping while the product is in use, thus eliminating any staining problem and concentrating iodine inside the cap.

Concept 3

Post Assembly Impregnation Process

Here, the cap disk concept is used as before, but instead of preimpregnation of the disk, elemental iodine is added to the system at the point of assembly. A small amount of iodine is dispensed into the cap and a disk is placed on top of the iodine capturing the iodine between the two components. The assembly is then packaged and the iodine impregnates the disk while in the package prior to reaching the customer. (Impregnation would probably be complete within one week.) This assembly method eliminates the need for impregnation equipment, and eliminates the inventory of disks that are held up during an impregnation process. Also, iodine gas containment is greatly simplified. Antimicrobial effectiveness of this configuration was tested and proved to be effective.

Concept 4

Solvent Dispensed Iodine Impregnation

Figure 16:
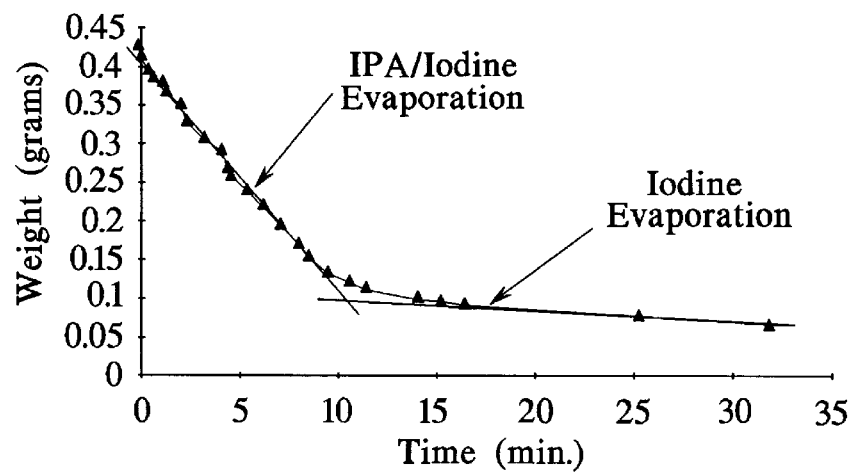
FIG. 16 illustrates the vapor rates by weight (g) versus time (min) of alcohol and iodine from an iodine solution.

The assembly process from concept 3 is used except that the elemental iodine is dissolved in a solvent, such as isopropyl alcohol (IPA), and volumetrically dispensed into the cap. The disk is then placed over the iodine solution and the assembly is packaged. The alcohol quickly evaporates into the package and the iodine, now dry, begins to diffuse into the disk. FIG. 16 illustrates the two distinct vaporation rates by weight versus time of alcohol and the iodine from the solution.

Incorporating the iodine solution into the manufacturing process allows for the dispensing of small amounts of iodine at production speeds. Moreover, it utilizes much of the current manufacturing equipment and technology in standard plants, thereby decreasing the capital costs of producing the product. Over time, the disconnect cap will release iodine gas to disinfect mating components. This design advantageously eliminates the liquid medium and maintains antimicrobial effectiveness.

By way of example, and not limitation, experiments demonstrating the feasibility of impregnating a plastic component of a dialysis disconnect cap with iodine as well as the effectiveness of same to kill viruses will now be given.

Experiment No. 10

This experiment demonstrated the ability to impregnate Hytrel® cap samples with iodine. The experiment also examined the rate of release of iodine from the samples. Still further, this experiment evaluated the mechanical stability of the iodine impregnated caps and the effectiveness of same to inactivate viruses.

Iodine Absorption study:

Hytrel® samples were utilized for testing in this experiment. Specifically, three sample jars with nine samples in each jar were utilized.

Prior to placing the samples in the three jars, the weight of each sample was recorded. Approximately 2.5 g of iodine was placed in a small filter paper pouches. Next, nine weighed samples were placed in each jar and an iodine pouch was placed in the neck of each jar. The cover on each jar was then tightly closed to create an enclosed vessel.

Figure 17:
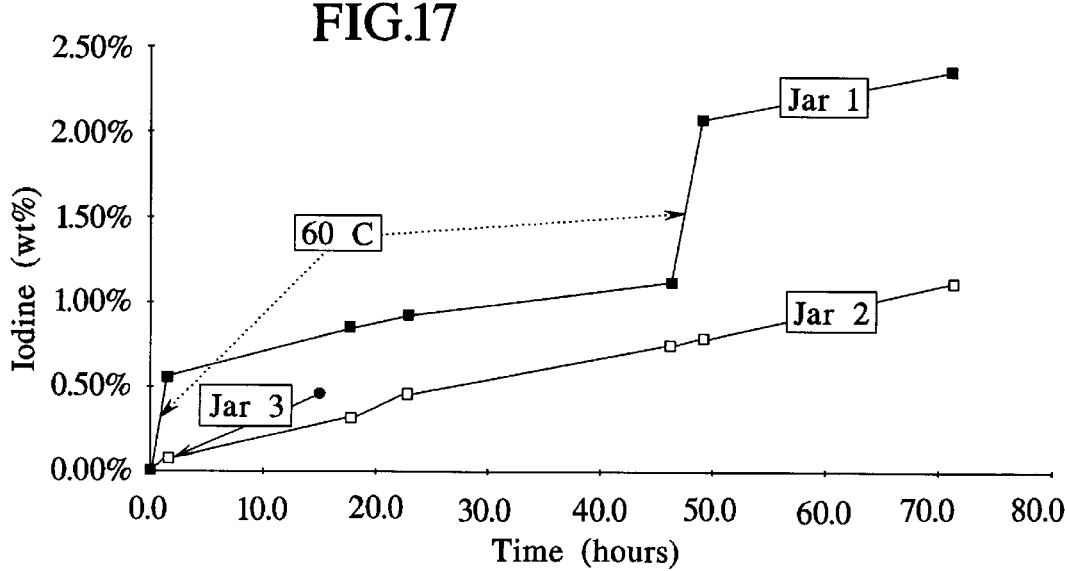
FIG. 17 illustrates the absorption of iodine into various samples in three testing jars by iodine weight percentage versus time.

The time and temperature of exposure was recorded for each sample in each jar. To determine the amount of iodine content, each sample was periodically weighed and changes were recorded. Tables 11A–13 detail the results from this absorption study. FIG. 17 illustrates the iodine absorption for the samples in the three jars by iodine weight percentage versus time. The samples in jar 1 were exposed to iodine for 72 hours at approximately 60° C. and absorbed 2.29% iodine by weight. The samples in jars 2 and 3 were exposed at approximately 27° C. for 72 hours and 13 hours, absorbing 1.06% and 0.43% iodine, respectively.

TABLE 11A

| Jar #1 Sample # | Time (hrs) Temp. Weight (gm) | 0.0 60° C. Iodine wt. % | Time (hrs) Temp. Weight (gm) | 1.5 27° C. Iodine wt. % | Time (hrs) Temp. Weight (gm) | 17.7 27° C. Iodine wt. % | Time (hrs) Temp. Weight (gm) | 22.9 27° C. Iodine wt. % |
|---|---|---|---|---|---|---|---|---|
| 28 | 1.9125 | 0.00% | 1.9263 | 0.72% | 1.9300 | 0.92% | 1.9316 | 1.00% |
| 16 | 1.9165 | 0.00% | 1.9274 | 0.57% | 1.9325 | 0.83% | 1.9340 | 0.91% |
| 4 | 1.9101 | 0.00% | 1.9183 | 0.43% | 1.9232 | 0.69% | 1.9251 | 0.79% |
| 18 | 1.9111 | 0.00% | 1.9213 | 0.53% | 1.9278 | 0.87% | 1.9288 | 0.93% |
| 12 | 1.9128 | 0.00% | 1.9248 | 0.63% | 1.9303 | 0.91% | 1.9311 | 0.96% |
| 13 | 1.9115 | 0.00% | 1.9205 | 0.47% | 1.9256 | 0.74% | 1.9270 | 0.81% |
| 20 | 1.9125 | 0.00% | 1.9215 | 0.47% | 1.9282 | 0.82% | 1.9300 | 0.92% |
| 31 | 1.9095 | 0.00% | 1.9172 | 0.40% | 1.9242 | 0.40% | 1.9255 | 0.84% |
| 19 | 1.9095 | 0.00% | 1.9226 | 0.69% | 1.9265 | 0.89% | 1.9288 | 1.01% |
| Average | | 0.00% | | 0.55% | | 0.83% | | 0.91% |
| Std. Dev. | | 0.0000 | | 0.0011 | | 0.0008 | | 0.0007 |

TABLE 11B

| Jar #1 Sample # | Time (hrs) Temp. Weight (gm) | 46.6 27° C. Iodine wt. % | Time (hrs) Temp. Weight (gm) | 49.5 60° C. Iodine wt. % | Time (hrs) Temp. Weight (gm) | 71.6 27° C. Iodine wt. % |
|---|---|---|---|---|---|---|
| 28 | 1.9343 | 1.14% | 1.9508 | 2.00% | 1.9551 | 2.23% |
| 16 | 1.9372 | 1.08% | 1.9598 | 2.26% | 1.9630 | 2.43% |
| 4 | 1.9284 | 0.96% | 1.9475 | 1.96% | 1.9522 | 2.21% |
| 18 | 1.9328 | 1.13% | 1.9498 | 2.02% | 1.9556 | 2.33% |
| 12 | 1.9349 | 1.15% | 1.9503 | 1.96% | 1.9563 | 2.27% |
| 13 | 1.9312 | 1.03% | 1.9464 | 1.83% | 1.9518 | 2.11% |
| 20 | 1.9336 | 1.10% | 1.9508 | 2.00% | 1.9569 | 2.32% |
| 31 | 1.9288 | 1.01% | 1.9475 | 1.99% | 1.9536 | 2.31% |
| 19 | 1.9325 | 1.21% | 1.9470 | 1.96% | 1.9547 | 2.37% |
| Average | | 1.09% | | 2.00% | | 2.29% |
| Std. Dev. | | 0.0007 | | 0.0011 | | 0.0009 |

TABLE 12A

| Jar #2 Sample # | Time (hrs) Temp. Weight (gm) | 0.0 27° C. Iodine wt. % | Time (hrs) Temp. Weight (gm) | 1.5 27° C. Iodine wt. % | Time (hrs) Temp. Weight (gm) | 17.7 27° C. Iodine wt. % | Time (hrs) Temp. Weight (gm) | 22.9 27° C. Iodine wt. % |
|---|---|---|---|---|---|---|---|---|
| 20 | 1.9112 | 0.00% | 1.9125 | 0.07% | 1.9161 | 0.26% | 1.9192 | 0.42% |
| 14 | 1.9095 | 0.00% | 1.9106 | 0.06% | 1.9157 | 0.32% | 1.9177 | 0.43% |
| 15 | 1.9173 | 0.00% | 1.9188 | 0.08% | 1.9233 | 0.31% | 1.9266 | 0.48% |
| 11 | 1.9180 | 0.00% | 1.9191 | 0.06% | 1.9236 | 0.29% | 1.9264 | 0.44% |
| 2 | 1.9153 | 0.00% | 1.9166 | 0.07% | 1.9218 | 0.34% | 1.9245 | 0.48% |
| 8 | 1.9121 | 0.00% | 1.9128 | 0.04% | 1.9168 | 0.25% | 1.9196 | 0.39% |
| 13 | 1.9124 | 0.00% | 1.9137 | 0.07% | 1.9185 | 0.32% | 1.9210 | 0.45% |
| 31 | 1.9089 | 0.00% | 1.9101 | 0.06% | 1.9139 | 0.26% | 1.9161 | 0.38% |
| 23 | 1.9133 | 0.00% | 1.9144 | 0.06% | 1.9192 | 0.31% | 1.9216 | 0.43% |
| Average | | 0.00% | | 0.06% | | 0.30% | | 0.43% |
| Std. Dev. | | 0.0000 | | 0.0001 | | 0.0003 | | 0.0003 |

TABLE 12B

| Jar #2 Sample # | Time (hrs) Temp. Weight (gm) | 46.3 27° C. Iodine wt. % | Time (hrs) Temp. Weight (gm) | 49.2 27° C. Iodine wt. % | Time (hrs) Temp. Weight (gm) | 71.4 27° C. Iodine wt. % |
|---|---|---|---|---|---|---|
| 20 | 1.9239 | 0.66% | 1.9244 | 0.69% | 1.9316 | 1.07% |
| 14 | 1.9237 | 0.74% | 1.9245 | 0.78% | 1.9312 | 1.14% |
| 15 | 1.9311 | 0.72% | 1.9322 | 0.78% | 1.9371 | 1.03% |
| 11 | 1.9317 | 0.72% | 1.9321 | 0.74% | 1.9376 | 1.02% |
| 2 | 1.9310 | 0.82% | 1.9316 | 0.85% | 1.9366 | 1.11% |
| 8 | 1.9244 | 0.64% | 1.9251 | 0.68% | 1.9305 | 0.96% |
| 13 | 1.9269 | 0.76% | 1.9266 | 0.74% | 1.9326 | 1.06% |
| 31 | 1.9231 | 0.74% | 1.9238 | 0.78% | 1.9298 | 1.09% |
| 23 | 1.9256 | 0.64% | 1.9271 | 0.72% | 1.9340 | 1.08% |
| Average |  | 0.72% |  | 0.75% |  | 1.06% |
| Std. Dev. |  | 0.0006 |  | 0.0005 |  | 0.0005 |

TABLE 13

| Jar #3 Sample # | Time (hrs) Temp. Weight (gm) | 0.0 27° C. Iodine wt. % | Time (hrs) Temp. Weight (gm) | 2.8 27° C. Iodine wt. % | Time (hrs) Temp. Weight (gm) | 13.3 27° C. Iodine wt. % |
|---|---|---|---|---|---|---|
| 12 | 1.9137 | 0.00% | 1.9161 | 0.13% | 1.9213 | 0.40% |
| 21 | 1.9219 | 0.00% | 1.9245 | 0.13% | 1.9300 | 0.42% |
| 18 | 1.9128 | 0.00% | 1.9149 | 0.11% | 1.9229 | 0.53% |
| 30 | 1.9111 | 0.00% | 1.9127 | 0.08% | 1.9200 | 0.47% |
| 31 | 1.9089 | 0.00% | 1.9111 | 0.11% | 1.9171 | 0.43% |
| 28 | 1.9124 | 0.00% | 1.9144 | 0.11% | 1.9225 | 0.53% |
| 8 | 1.9122 | 0.00% | 1.9144 | 0.11% | 1.9192 | 0.37% |
| 19 | 1.9098 | 0.00% | 1.9118 | 0.10% | 1.9170 | 0.38% |
| 15 | 1.9172 | 0.00% | 1.9188 | 0.08% | 1.9244 | 0.38% |
| Average |  | 0.00% |  | 0.11% |  | 0.43% |
| Std. Dev. |  | 0.0000 |  | 0.0002 |  | 0.0006 |

Figure 18A:
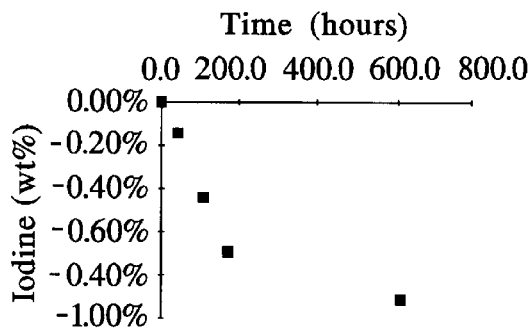
FIGS. 18A–18C illustrate the release of iodine from impregnated samples in testing Jar 1, Jar 2 and Jar 3, respectively, by iodine weight percentage versus time.
Figure 18B:
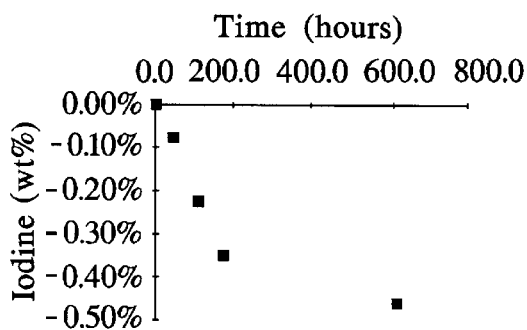
Figure 18C:
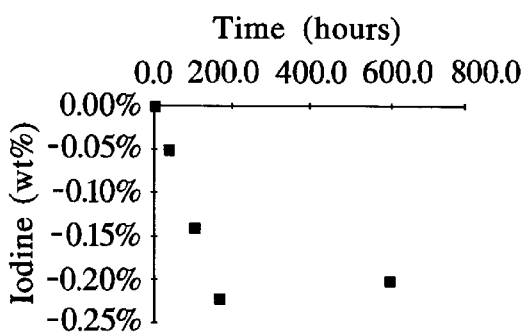

Iodine Release Study:

This study measured the rate of release of iodine from the samples prepared in the previous absorption study. To measure the iodine release, the samples were stored in an open plastic beaker under a fume hood to allow the iodine to escape from the Hytrel® material. The samples were weighed over time to determine the release rate. Tables 14A–16B detail the results of this study. FIGS. 18A–18C illustrate the release of iodine from the samples in Jar 1, Jar 2 and Jar 3, respectively, by iodine weight percentage versus time.

TABLE 14A

| Jar #1 Sample # | Time (hrs) Temp. Weight (gm) | 0.0 27° C. Iodine wt. % | Time (hrs) Temp. Weight (gm) | 31.0 27° C. Iodine wt. % | Time (hrs) Temp. Weight (gm) | 99.5 27° C. Iodine wt. % |
|---|---|---|---|---|---|---|
| 20 | 1.9562 | 0.00% | 1.9530 | -0.16% | 1.9473 | -0.45% |
| 19 | 1.9533 | 0.00% | 1.9505 | -0.14% | 1.9442 | -0.47% |
| 18 | 1.9546 | 0.00% | 1.9520 | -0.13% | 1.9448 | -0.50% |
| 4 | 1.9526 | 0.00% | 1.9496 | -0.15% | 1.9446 | -0.41% |
| 16 | 1.9621 | 0.00% | 1.9596 | -0.13% | 1.9526 | -0.48% |
| 13 | 1.9508 | 0.00% | 1.9479 | -0.15% | 1.9420 | -0.45% |
| 12 | 1.9552 | 0.00% | 1.9517 | -0.18% | 1.9450 | -0.52% |
| 28 | 1.9554 | 0.00% | 1.9520 | -0.17% | 1.9460 | -0.48% |
| 31 | 1.9524 | 0.00% | 1.9499 | -0.13% | 1.9441 | -0.43% |
| Average |  | 0.00% |  | -0.15% |  | -0.47% |
| Std. Dev. |  | 0.0000 |  | 0.0002 |  | 0.0003 |

TABLE 14B

| Jar #1 Sample # | Time (hrs) Temp. Weight (gm) | 147.8 27° C. Iodine wt. % | Time (hrs) Temp. Weight (gm) | 622.0 27° C. Iodine wt. % |
|---|---|---|---|---|
| 20 | 1.9435 | -0.65% | 1.9373 | -0.97% |
| 19 | 1.9406 | -0.65% | 1.9344 | -0.97% |
| 18 | 1.9413 | -0.68% | 1.9355 | -0.98% |
| 4 | 1.9414 | -0.58% | 1.9346 | -0.92% |
| 16 | 1.9492 | -0.66% | 1.9430 | -0.97% |
| 13 | 1.9391 | -0.60% | 1.9339 | -0.87% |
| 12 | 1.9419 | -0.68% | 1.9366 | -0.95% |
| 28 | 1.9429 | -0.64% | 1.9332 | -1.14% |
| 31 | 1.9405 | -0.61% | 1.9331 | -0.99% |
| Average |  | -0.64% |  | -0.97% |
| Std. Dev. |  | 0.0003 |  | 0.0007 |

TABLE 15A

| Jar #2 Sample # | Time (hrs) Temp. Weight (gm) | 0.0 27° C. Iodine wt. % | Time (hrs) Temp. Weight (gm) | 31.0 27° C. Iodine wt. % | Time (hrs) Temp. Weight (gm) | 99.5 27° C. Iodine wt. % |
|---|---|---|---|---|---|---|
| 14 | 1.9300 | 0.00% | 1.9282 | -0.09% | 1.9255 | -0.23% |
| 31 | 1.9303 | 0.00% | 1.9282 | -0.11% | 1.9247 | -0.29% |
| 8 | 1.9305 | 0.00% | 1.9285 | -0.10% | 1.9265 | -0.21% |
| 2 | 1.9357 | 0.00% | 1.9340 | -0.09% | 1.9312 | -0.23% |
| 15 | 1.9328 | 0.00% | 1.9342 | -0.07% | 1.9321 | -0.04% |
| 20 | 1.9312 | 0.00% | 1.9288 | -0.12% | 1.9259 | -0.27% |
| 13 | 1.9323 | 0.00% | 1.9302 | -0.11% | 1.9276 | -0.24% |
| 11 | 1.9374 | 0.00% | 1.9353 | -0.11% | 1.9321 | -0.27% |
| 23 | 1.9332 | 0.00% | 1.9311 | -0.11% | 1.9283 | -0.25% |
| Average |  | 0.00% |  | -0.09% |  | -0.23% |
| Std. Dev. |  | 0.0000 |  | 0.0006 |  | 0.0007 |

TABLE 15B

| Jar #2 Sample # | Time (hrs) Temp. Weight (gm) | 147.8 27° C. Iodine wt. % | Time (hrs) Temp. Weight (gm) | 622.0 27° C. Iodine wt. % |
|---|---|---|---|---|
| 14 | 1.9229 | -0.37% | 1.9209 | -0.47% |
| 31 | 1.9222 | -0.42% | 1.9178 | -0.65% |
| 8 | 1.9239 | -0.34% | 1.9223 | -0.42% |
| 2 | 1.9289 | -0.35% | 1.9265 | -0.48% |
| 15 | 1.9298 | -0.16% | 1.9278 | -0.26% |
| 20 | 1.9238 | -0.38% | 1.9219 | -0.48% |
| 13 | 1.9252 | -0.37% | 1.9232 | -0.47% |
| 11 | 1.9302 | -0.37% | 1.9285 | -0.46% |
| 23 | 1.9263 | -0.36% | 1.9245 | -0.45% |
| Average |  | -0.35% |  | -0.46% |
| Std. Dev. |  | 0.0007 |  | 0.0009 |

TABLE 16A

| Jar #3 Sample # | Time (hrs) Temp. Weight (gm) | 0.0 27° C. Iodine wt. % | Time (hrs) Temp. Weight (gm) | 31.0 27° C. Iodine wt. % | Time (hrs) Temp. Weight (gm) | 99.5 27° C. Iodine wt. % |
|---|---|---|---|---|---|---|
| 12 | 1.9224 | 0.00% | 1.9216 | -0.04% | 1.9199 | -0.13% |
| 18 | 1.9229 | 0.00% | 1.9215 | -0.07% | 1.9164 | -0.34% |
| 15 | 1.9251 | 0.00% | 1.9243 | -0.04% | 1.9227 | -0.12% |
| 28 | 1.9221 | 0.00% | 1.9206 | -0.08% | 1.9191 | -0.16% |
| 19 | 1.9170 | 0.00% | 1.9163 | -0.04% | 1.9152 | -0.09% |
| 30 | 1.9199 | 0.00% | 1.9186 | -0.07% | 1.9175 | -0.13% |

TABLE 16A-continued

| Jar #3 Sample # | Time (hrs) 0.0 Temp. 27° C. Weight (gm) | 27° C. Iodine wt. % | Time (hrs) 31.0 Temp. 27° C. Weight (gm) | 27° C. Iodine wt. % | Time (hrs) 99.5 Temp. 27° C. Weight (gm) | 27° C. Iodine wt. % |
| --- | --- | --- | --- | --- | --- | --- |
| 21 | 1.9301 | 0.00% | 1.9292 | −0.05% | 1.9284 | −0.09% |
| 8 | 1.9197 | 0.00% | 1.9193 | −0.02% | 1.9179 | −0.09% |
| 31 | 1.9173 | 0.00% | 1.9160 | −0.07% | 1.9147 | −0.14% |
| Average | | 0.00% | | −0.05% | | −0.14% |
| Std. Dev. | | 0.0000 | | 0.0002 | | 0.0007 |

TABLE 16B

| Jar #3 Sample # | Time (hrs) Temp. Weight (gm) | 147.8 27° C. Iodine wt. % | Time (hrs) Temp. Weight (gm) | 622.0 27° C. Iodine wt. % |
| --- | --- | --- | --- | --- |
| 12 | 1.9180 | −0.22% | 1.9187 | −0.19% |
| 18 | 1.9179 | −0.26% | 1.9183 | −0.24% |
| 15 | 1.9209 | −0.22% | 1.9214 | −0.19% |
| 28 | 1.9173 | −0.25% | 1.9157 | −0.33% |
| 19 | 1.9135 | −0.18% | 1.9140 | −0.16% |
| 30 | 1.9156 | −0.22% | 1.9160 | −0.20% |
| 21 | 1.9265 | −0.19% | 1.9267 | −0.18% |
| 8 | 1.9157 | −0.21% | 1.9167 | −0.16% |

TABLE 16B-continued

| Jar #3 Sample # | Time (hrs) Temp. Weight (gm) | 147.8 27° C. Iodine wt. % | Time (hrs) Temp. Weight (gm) | 622.0 27° C. Iodine wt. % |
| --- | --- | --- | --- | --- |
| 31 | 1.9132 | −0.21% | 1.9136 | −0.19% |
| Average | | −0.22% | | −0.20% |
| Std. Dev. | | 0.0002 | | 0.0005 |

Mechanical Testing Study:

This study measured the tensile properties of the samples prepared in the previous absorption study. The same control group utilized in the absorption study was also used as a control in this study. Each of the samples were evaluated based on a pull test on an Instrom tensile tester.

Tables 17–20 detail the results of this study. Table 17 shows testing results on the control group, dry unimpregnated Hytrel® samples. Table 18 shows testing results on Hytrel® samples impregnated with 0.43% dry iodine. Table 19 shows testing results on Hytrel® samples impregnated with 1.06% dry iodine. Lastly, table 20 shows testing results on Hytrel® samples impregnated with 2.29% dry iodine.

TABLE 17

Unimpregnated Hytrel ® -control group

| Specimen Number | Peak Load (lbs) | Break Load (lbs) | Elongation at Break (in) | % Strain at Auto. Break (%) | Displacement at Thresh Yield (in) |
| --- | --- | --- | --- | --- | --- |
| 1 | 126.8 | 126.6 | 5.170 | 1034.0 | .4474 |
| 2 | 123.9 | 123.9 | 4.990 | 998.0 | .4649 |
| 3 | 116.7 | 116.7 | 4.810 | 962.0 | .4849 |
| 4 | 126.9 | 126.9 | 5.100 | 1020.0 | .4776 |
| 5 | 117.8 | 117.6 | 4.770 | 954.0 | .4515 |
| 6 | 123.8 | 123.7 | 4.980 | 996.0 | .4450 |
| 7 | 125.4 | 125.3 | 5.070 | 1014.0 | .4615 |
| 8 | 126.2 | 126.2 | 5.200 | 1040.0 | .4615 |
| 9 | 122.2 | 122.2 | 4.970 | 994.0 | .4687 |
| Mean: | 123.3 | 123.2 | 5.007 | 1001.0 | .4625 |
| Standard Derivation: | 3.8 | 3.8 | .147 | 29.5 | .0134 |
| Minimum: | 116.7 | 116.7 | 4.770 | 954.0 | .4450 |
| Maximum: | 126.9 | 126.9 | 5.200 | 1040.0 | .4849 |

TABLE 18

Hytrel ® Impregnated with .43% dry iodine

| Specimen Number | Peak Load (lbs) | Break Load (lbs) | Elongation at Break (in) | % Strain at Auto. Break (%) | Displacement at Thresh Yield (in) |
| --- | --- | --- | --- | --- | --- |
| 1 | 119.10 | 118.90 | 4.960 | 992.0 | .4646 |
| 2 | 117.70 | 117.40 | 4.990 | 980.0 | .4983 |
| *Excluded* | 60.50 | 59.15 | 2.430 | 486.0 | .5150 |
| 4 | 121.70 | 121.70 | 5.070 | 1014.0 | .4646 |
| 5 | 118.80 | 118.50 | 4.930 | 986.0 | .4781 |
| 6 | 126.70 | 126.60 | 5.300 | 1060.0 | .4781 |
| 7 | 120.70 | 120.70 | 5.060 | 1012.0 | .4853 |
| 8 | 116.00 | 115.80 | 4.860 | 972.0 | .4937 |
| 9 | 117.80 | 117.80 | 4.930 | 986.0 | .4944 |
| Mean: | 119.80 | 119.70 | 5.001 | 1000.0 | .4821 |
| Standard | 3.30 | 3.36 | .141 | 28.2 | .0131 |

TABLE 18-continued

Hytrel ® Impregnated with .43% dry iodine

| Specimen Number | Peak Load (lbs) | Break Load (lbs) | Elongation at Break (in) | % Strain at Auto. Break (%) | Displacement at Thresh Yield (in) |
| --- | --- | --- | --- | --- | --- |
| Derivation | | | | | |
| Minimum: | 116.0 | 115.80 | 4.860 | 972.0 | .4646 |
| Maximum: | 126.70 | 126.60 | 5.300 | 1060.0 | .4983 |

TABLE 19

Hytrel ® Impregnated with 1.06% dry iodine

| Specimen Number | Peak Load (lbs) | Break Load (lbs) | Elongation at Break (in) | % Strain at Auto. Break (%) | Displacement at Thresh Yield (in) |
| --- | --- | --- | --- | --- | --- |
| 1 | 124.8 | 124.8 | 5.270 | 1054.0 | .4777 |
| 2 | 123.2 | 123.0 | 5.220 | 1044.0 | .4784 |
| 3 | 119.7 | 119.7 | 5.040 | 1008.0 | .4683 |
| 4 | 111.4 | 111.4 | 4.770 | 954.0 | .4659 |
| 5 | 122.8 | 122.5 | 5.110 | 1022.0 | .4691 |
| 6 | 119.5 | 119.3 | 4.990 | 998.0 | .4656 |
| 7 | 117.1 | 117.0 | 4.920 | 984.0 | .4822 |
| 8 | 118.6 | 118.4 | 5.020 | 1004.0 | .4786 |
| 9 | 118.2 | 118.2 | 4.950 | 990.0 | .4822 |
| Mean: | 119.5 | 119.4 | 5.032 | 1006.0 | .4742 |
| Standard Derivation: | 4.0 | 3.9 | .153 | 30.7 | .0069 |
| Minimum: | 111.4 | 111.4 | 4.770 | 954.0 | .4656 |
| Maximum: | 124.8 | 124.8 | 5.270 | 1054.0 | .4822 |

TABLE 20

Hytrel ® Impregnated with 2.29% dry iodine

| Specimen Number | Peak Load (lbs) | Break Load (lbs) | Elongation at Break (in) | % Strain at Auto. Break (%) | Displacement at Thresh Yield (in) |
| --- | --- | --- | --- | --- | --- |
| 1 | 110.6 | 110.5 | 5.110 | 1022.0 | .4688 |
| 2 | 111.6 | 111.5 | 5.140 | 1028.0 | .4822 |
| 3 | 105.9 | 105.8 | 4.820 | 964.0 | .4786 |
| 4 | 104.0 | 104.0 | 4.900 | 980.0 | .4654 |
| 5 | 107.3 | 107.1 | 4.930 | 986.0 | .4822 |
| 6 | 113.5 | 113.3 | 5.040 | 1008.0 | .4825 |
| 7 | 103.9 | 103.9 | 4.760 | 952.0 | .4782 |
| 8 | 104.5 | 104.5 | 4.870 | 974.0 | .4822 |
| 9 | 113.0 | 113.0 | 5.140 | 1028.0 | .4825 |
| Mean: | 108.3 | 108.2 | 4.968 | 993.6 | .4781 |
| Standard Derivation: | 3.9 | 3.9 | .144 | 28.8 | .0065 |
| Minimum: | 103.9 | 103.9 | 4.760 | 952.0 | .4654 |
| Maximum: | 113.5 | 113.3 | 5.140 | 1028.0 | .4825 |

Based on these mechanical testing methods, iodine was found to not adversely affect the elongation at break. However, the break force decreased slightly in the 2.29% iodine caps. The inventors believe this result is possibly due to the 60° F. temperature exposure during absorption.

Antibacterial Effectiveness Study:

To measure the ability of the impregnated plastic components to eliminate microorganisms, two experimental analyses were conducted. The first experiment used the impregnated caps prepared in the prior absorption study to disinfect approximately $10^5$ colony forming units of *Staphylococcus aureus* bacteria.

Connecting devices were purposely contaminated with $10^5$ cfu (colony forming units) of *S. aureus*. Caps impregnated with the three levels of iodine were then placed onto the connecting devices and left on for one hour. After one hour, the caps were removed and the connecting devices placed into bacteriological growth medium containing an iodine inactivating agent to halt any continuing bactericidal activity. The media were incubated at 35° C. and observed for growth of *S. aureus*. The results are displayed in Table 21.

TABLE 21

| Test Samples | #samplesshowingtotaldisinfection / # samples tested |
|---|---|
| Group 1 | 7/7 |
| Group 2 | 7/7 |
| Group 3 | 6/7 |

The second experiment evaluated the antimicrobial efficacy of iodine impregnated plastic disks placed at the bottom of the caps as opposed to iodine impregnated caps. The test design was essentially the same as for impregnated caps. Test results indicated that the iodine vapors from the disks were sufficient to disinfect the connecting devices.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A release material comprising:

a two layer structure comprising a first layer connected to a second layer;

the first layer comprising a first plastic material having impregnated therein a halogen, the first plastic material and the halogen defining an outer surface facing a first direction and having a first release rate in the first direction for the halogen;

the second layer comprising a second plastic material that is different than the first plastic material, having impregnated therein the halogen, the second plastic material and the halogen defining an inner surface facing a second direction and having a second release rate for the halogen, the second release rate in the second direction being faster than the first release rate in the first direction to achieve directional release of the halogen.

2. The release material of claim 1 wherein the first and the second plastic material are each chosen from the group consisting of: polyethylene; polyurethane; polypropylene; polystyrene; copolyester; polycarbonate/polyester blend and styrene-ethylene-butylene-styrene copolymers.

3. The release material of claim 1 wherein approximately 0 to 40% of the halogen is impregnated in each of the first and the second plastic material.

4. The release material of claim 1 wherein the halogen is iodine.

* * * * *

UNITED STATES PATENT AND TRADEMARK OFFICE
CERTIFICATE OF CORRECTION

PATENT NO. : 5,948,385

DATED : September 7, 1999

INVENTOR(S) : John R. Chapman, et al.

It is certified that error appears in the above-identified patent and that said Letters Patent is hereby corrected as shown below:

Column 2, Line 9: delete "completed" and insert --complexed--

Signed and Sealed this

Eighteenth Day of April, 2000

Attest:

Q. TODD DICKINSON

*Attesting Officer*      *Director of Patents and Trademarks*